US008664615B2

(12) United States Patent
Amitani et al.

(10) Patent No.: US 8,664,615 B2
(45) Date of Patent: Mar. 4, 2014

(54) RADIATION IMAGE CAPTURING DEVICE

(75) Inventors: Kouji Amitani, Tachikawa (JP); Hideaki Tajima, Hachioji (JP); Kaneyuki Nakano, Hino (JP)

(73) Assignee: Konica Minolta Medical & Graphic, Inc. (JP)

( * ) Notice: Subject to any disclaimer, the term of this patent is extended or adjusted under 35 U.S.C. 154(b) by 191 days.

(21) Appl. No.: 13/388,870

(22) PCT Filed: Feb. 8, 2010

(86) PCT No.: PCT/JP2010/051753
§ 371 (c)(1),
(2), (4) Date: Feb. 3, 2012

(87) PCT Pub. No.: WO2011/016262
PCT Pub. Date: Feb. 10, 2011

(65) Prior Publication Data
US 2012/0132825 A1 May 31, 2012

(30) Foreign Application Priority Data

Aug. 7, 2009 (JP) .................................. 2009-183928
Aug. 13, 2009 (JP) .................................. 2009-187632

(51) Int. Cl.
*G01T 1/24* (2006.01)
(52) U.S. Cl.
USPC .................................................... 250/370.09
(58) Field of Classification Search
USPC .................................................... 250/370.09
See application file for complete search history.

(56) References Cited

U.S. PATENT DOCUMENTS 7,211,803 B1  5/2007  Dhurjaty et al.
2003/0086523 A1  5/2003  Tashiro et al.

FOREIGN PATENT DOCUMENTS

| JP | 6-342099 A | 12/1994 |
| JP | 9-73144 A | 3/1997 |
| JP | 11-155847 A | 6/1999 |
| JP | 2003-126072 A | 5/2003 |
| JP | 2006-58124 A | 3/2006 |
| WO | 2009/075172 A1 | 6/2009 |

OTHER PUBLICATIONS

International Search Report for International Application No. PCT/JP2010/051753, mailed Mar. 16, 2012, with English translation.

*Primary Examiner* — David Porta
*Assistant Examiner* — Hugh H Maupin
(74) *Attorney, Agent, or Firm* — Cantor Colburn LLP

(57) ABSTRACT

Disclosed is a radiation image capturing device including a control section which detects at least a start of irradiation based on a current value of a current detected by a current detection section, wherein the control section applies an ON-state voltage having a predetermined voltage value from a scan driving section to a switch section via each of scan lines simultaneously so as to perform reset processing of each of radiation detection elements before radiation image capturing, and thereafter, decreases the voltage value of the ON-state voltage simultaneously, monitors the current value outputted from the current detection section while keeping the decreased voltage value of the ON-state voltage, and waits for the start of the irradiation.

12 Claims, 22 Drawing Sheets

RADIATION IMAGE CAPTURING DEVICE

CROSS REFERENCE TO RELATED APPLICATIONS

This is a U.S. national stage of application No. PCT/JP2010/051753, filed on Feb. 8, 2010. Priority under 35 U.S.C. §119(a) and 35 U.S.C. §365(b) is claimed from Japanese Application Nos. 2009-183928, filed Aug. 7, 2009, and 2009-187632, filed on Aug. 13, 2009, and the disclosure of which is also incorporated herein by reference.

TECHNICAL FIELD

The present invention relates to a radiation image capturing device, and in particular, relates to a radiation image capturing device which can detect the start of irradiation and the like by itself.

BACKGROUND OF THE ART

Various types of radiation image capturing devices such as a so-called direct-type radiation image capturing device and a so-called indirect-type radiation image have been developed. The direct-type radiation image capturing device generates electric charge with a detection element in accordance with the dose of radiation such as X-rays, and converts the generated charge into electric signals. The indirect-type radiation image capturing device converts radiation with a scintillator or the like into electromagnetic waves having a different wavelength from the radiation such as visible light, generates charge with a photoelectric conversion element such as a photodiode in accordance with the energy of the converted electromagnetic waves thereafter, and converts the generated charge into electric signals. In the present invention, the detection element in the direct-type radiation image capturing device and the photoelectric conversion element in the indirect-type radiation image capturing device are referred to as radiation detection elements.

Each of these types of radiation image capturing devices is known as an FPD (Flat Panel Detector), and is conventionally formed to be united with a supporting stand (or a Bucky device). (Refer to Patent Document 1, for example.) However, in recent years, a portable radiation image capturing device including a radiation detection element and the like housed in a housing has been developed and in practical use. (Refer to Patent Documents 2 and 3, for example.)

By the way, among these types of radiation image capturing devices, in particular, some portable radiation image capturing device is configured to read image data from radiation detection elements after irradiation is performed, in response to the information on the start and/or the end of the irradiation transmitted from an external device, such as a computer, which manages an irradiation device or a system.

However, to do that, it is necessary to interface a radiation image capturing device with an irradiation device, a computer, or the like, and build a control configuration of a system including the irradiation device, the computer, or the like, as a whole. Hence, the configuration of the radiation image capturing device to recognize the start and/or the end of irradiation becomes on a large-scale. Therefore, it is desired that a radiation image capturing device is configured to be able to detect the start and/or the end of irradiation by itself.

In order to make a radiation image capturing device detect the start and the like of irradiation by itself, the radiation image capturing device may be configured to include a sensor and the like, and detect the start and/or the end of irradiation with the sensor. However, in this case, a space to provide the sensor is needed in the radiation image capturing device, and hence the radiation image capturing device becomes larger. In addition, when a sensor is provided therein, more power is consumed for the sensor to be driven. This is a problem particularly for a portable radiation image capturing device because a built-in battery thereof is consumed.

Hence, as shown in FIG. 7 described below, for example, it is proposed to detect current flowing in bias lines 9 for applying a bias voltage from a bias power supply 14 to radiation detection elements, or detect current flowing in a connection line 10 for the bias lines 9, and, by utilizing the fact that when the radiation detection elements are irradiated, electron-hole pairs are generated in the irradiated radiation detection elements and the current flows in the bias lines 9, detect the start and/or the end of irradiation from the increase and/or the decrease of the current value of the current. (Refer to Patent Document 4, for example.)

As described above, in the case where the current flowing in the bias lines 9 and/or the connection line 10 is detected so that the start and/or the end of the irradiation is detected from the increase and/or the decrease of the current value, the current flowing in the bias lines 9 and/or the connection line 10 accompanying the irradiation easily flows therein when switch sections of TFTs 8 (Thin Film Transistor, shown in FIG. 7 and the like) connected to radiation detection elements are on so that the gates of the TFTs 8 are opened.

Hence, some radiation image capturing device is configured to monitor the current flowing in the bias lines 9 or the like with the TFTs 8 on, and detect the start of the irradiation by detecting the increase of the current. Note that, if, after the start of the irradiation is detected, the TFTs 8 are kept on, charge (image data) generated in the radiation detection elements 7 by irradiation is discharged from the radiation detection elements 7. Hence, in order to switch to a mode in which the charge (image data) is accumulated, the TFTs 8 are turned off.

RELATED ART DOCUMENTS

Patent Documents
Patent Document 1: Japanese Patent Application Laid-Open Publication No. hei 9-73144
Patent Document 2: Japanese Patent Application Laid-Open Publication No. 2006-058124
Patent Document 3: Japanese Patent Application Laid-Open Publication No. hei 6-342099
Patent Document 4: U.S. Pat. No. 7,211,803

SUMMARY OF THE INVENTION

Problems to be Solved by the Invention

However, in a radiation image capturing device 100 configured to detect the current flowing in the bias lines 9 and/or the connection line 10 when irradiation starts, so as to detect the start of the irradiation as described above, for example, as shown in FIG. 23A, when a region R1 which is a part of a surface R receiving radiation (radiation incidence surface R, hereinbelow) is exposed to strong radiation, and the other regions thereof are not exposed to the radiation, as shown in FIG. 23B, there is a case where, in the obtained radiation image, while the region R1 exposed to the strong radiation is captured in black, among the other regions not exposed to the radiation, regions R2 adjacent to the region R1 exposed to the strong radiation are captured somewhat in black too.

This phenomenon can be seen even after image adjustment processing such as offset correction is performed. This indicates that although the radiation detection elements 7 existing in the regions R2 are not exposed to radiation, the regions R2 being adjacent to the region R1 exposed to strong radiation, image data having a significant value, namely, not "0", is generated therein, because the region R1 adjacent to the regions R2 is exposed to the strong radiation.

Furthermore, the above-described phenomenon may occur in a case where a region R1 including a subject H of a hand of a patient or the like is exposed to radiation so that a radiation image is captured, as shown in FIG. 24A. That is, when the radiation image capturing is performed in such a way, in a region Rh, in which the subject H is photographed, of the obtained radiation image, an image of the bone structure or the internal tissue of the hand of the patient is captured. However, as shown in FIG. 24B, because of the region R1 around the subject H and directly exposed to radiation, in addition to the image data obtained by capturing an image of information on the internal tissue and the like, image data having a significant value of not 0 is generated in a region Rh adjacent to the region R1.

The image data having a significant value obtained by the influence of the region R1 around the subject H and directly exposed to radiation overlays the image of the internal tissue and the like of the subject H. Consequently, the image of the internal tissue and the like of the subject H becomes blackish. As a result, for example, a lesioned part which is originally hard to be seen in a radiation image becomes more difficult to be seen. Hence, it may be difficult for a doctor or the like to judge whether or not there is a lesioned part.

When a radiation image capturing device is used to capture an image of a lesioned part for diagnosis or the like, it is desired that an image region in which an image of a subject is captured is appropriately prevented from being influenced by a region which is located around the image region and directly exposed to radiation.

The present invention is made in view of the problems, and an object of the present invention is to provide a radiation image capturing device which can appropriately prevent an image region in which an image of a subject is captured from being influenced by a region directly exposed to radiation.

Means for Solving the Problems

In order to solve the above-described problems, a radiation image capturing device according to the present invention is a radiation image capturing device including: a detection section including: a plurality of scan lines; a plurality of signal lines arranged to intersect the scan lines; and a plurality of radiation detection elements two-dimensionally and respectively arranged in a plurality of regions divided by the scan lines and the signal lines; a switch section provided for each of the radiation detection elements, wherein when an ON-state voltage is applied to the scan lines to which the switch section is connected, the switch section discharges electric charge generated in the radiation detection elements, and when an OFF-state voltage is applied to the connected scan lines, the switch section accumulates the electric charge in the radiation detection elements, the electric charge being generated in the radiation detection elements; a scan driving section including: a gate driver which applies a voltage to the switch section via each of the scan lines; and a power supply circuit which supplies the voltage to the gate driver; a current detection section which detects a current flowing in the device by irradiation; and a control section which detects at least a start of the irradiation based on a current value of the current detected by the current detection section, wherein the control section applies the ON-state voltage having a predetermined voltage value from the scan driving section to the switch section via each of the scan lines simultaneously so as to perform reset processing of each of the radiation detection elements before radiation image capturing, and thereafter, decreases the voltage value of the ON-state voltage simultaneously, monitors the current value outputted from the current detection section while keeping the decreased voltage value of the ON-state voltage, and waits for the start of the irradiation.

Advantageous Effects of the Invention

According to the radiation image capturing device of the present invention, by, first, applying the ON-state voltage having a high voltage value to the switch section all at once, and making the situation in which electric charge is easily discharged from the radiation detection elements, excess charge such as dark charge accumulated in the radiation detection elements can be discharged therefrom for sure, and hence the reset efficiency of the radiation detection elements can be increased.

Furthermore, the irradiation starts by switching the ON-state voltage being applied to the ON-state voltage having a low voltage value thereafter, and the charge discharged from the radiation detection elements when the charge starts to be generated in the radiation detection elements by irradiation, namely, the current value, can be controlled not to be too large. Because the current discharged from the radiation detection elements is controlled, the fluctuation of the voltage applied to the electrodes of the radiation detection elements can be prevented from occurring, the fluctuation which may occur in accordance with the current amount.

Therefore, non-irradiated radiation detection elements which are connected to the signal line and the bias line to which the irradiated radiation detection elements is connected, but not exposed to radiation (namely, the radiation detection elements in the regions R2 of FIG. 23B, for example) or weakly-irradiated radiation detection elements which are connected to the signal line and the like to which directly-irradiated radiation detection elements are connected, and exposed to weak radiation passing through the subject H (i.e. the radiation detection elements in the region Rh of FIG. 24B, for example) can be appropriately prevented from being influenced by the region R1 located near the non-irradiated radiation detection elements and exposed to strong radiation or the region R1 located near the weakly-irradiated radiation detection elements and directly exposed to radiation.

Furthermore, for example, a captured image of the bone structure or the internal tissue of a hand of a patient in the region Rh in which the subject H of the hand of the patient is photographed as shown in FIG. 24A is not influenced by the region R1 located near the region Rh and directly exposed to radiation. Consequently, the region Rh is prevented from being blackish. Therefore, for example, a lesioned part which is originally hard to be seen in a radiation image can be captured with excellent contrast. Hence, a doctor or the like can appropriately judge whether there is a lesioned part or not.

BRIEF DESCRIPTION OF THE DRAWINGS

FIG. 6 is a lateral view for explaining the substrate provided with a COF, a PCB substrate, and the like;

BEST MODE FOR CARRYING OUT THE INVENTION

In the following, a radiation image capturing device according to embodiments of the present invention is described with reference to the drawings.

In the following, the radiation image capturing device is described as the so-called indirect-type radiation image capturing device which obtains electrical signals by converting radiation, to which the radiation image capturing device is exposed, into electromagnetic waves having a wavelength different from the wavelength of the radiation, such as visible light, the indirect-type radiation image capturing device including a scintillator. However, the present invention can be applied to the direct-type radiation image capturing device. Furthermore, the radiation image capturing device is described as a portable radiation image capturing device. However, the present invention can be applied to a radiation image capturing device which is formed to be united with a supporting member or the like.

First Embodiment

Figure 1:
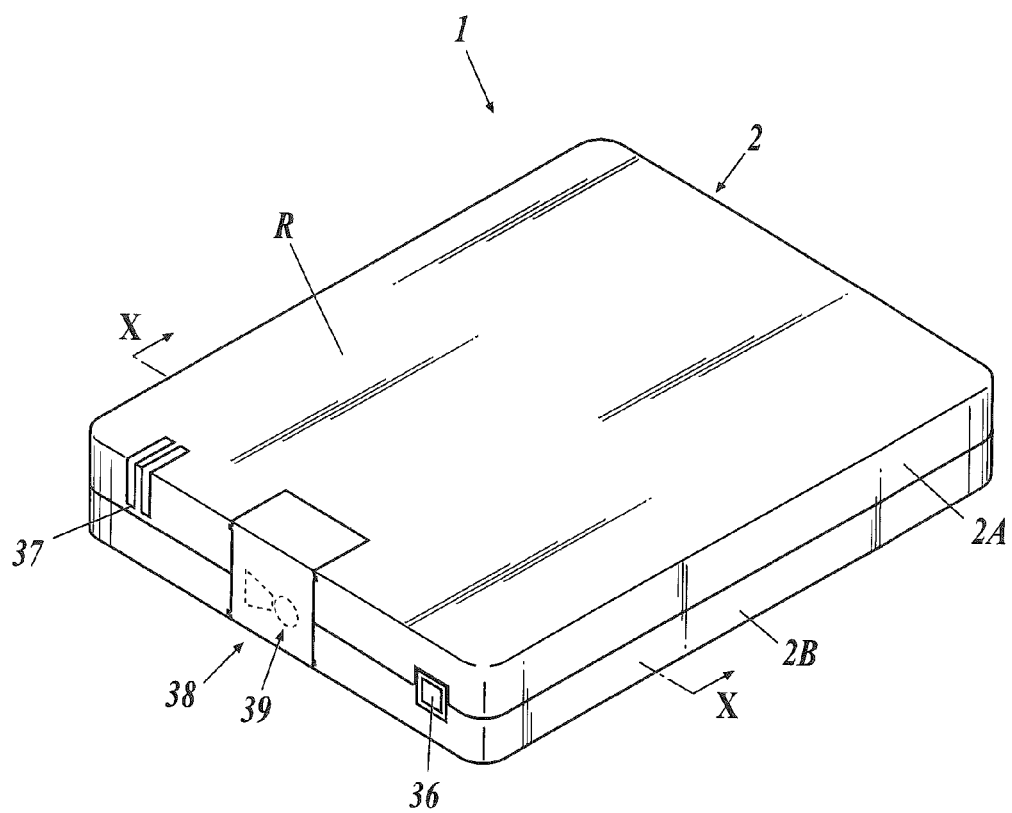
FIG. 1 is a perspective view of a radiation image capturing device according to each embodiment of the present invention.
Figure 2:
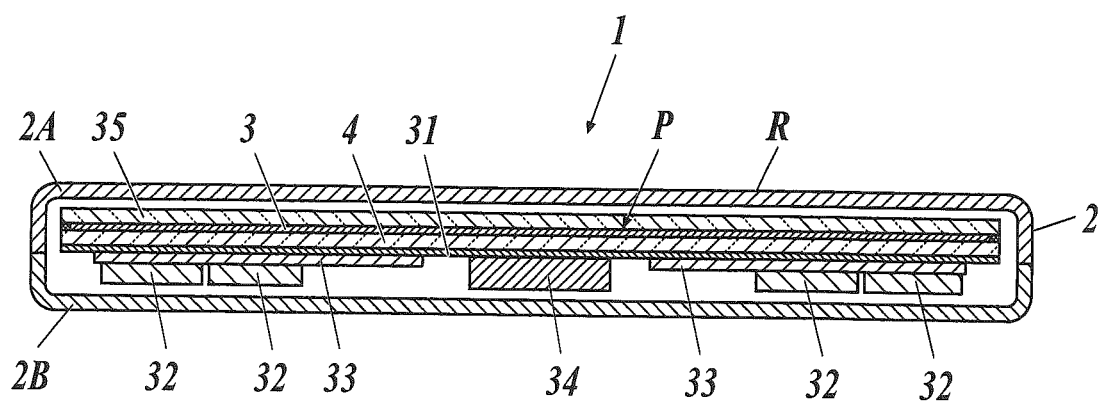
FIG. 2 is a sectional view taken along the line X-X of FIG. 1.

FIG. 1 is a perspective view showing the external appearance of a radiation image capturing device according to a first embodiment of the present invention. FIG. 2 is a sectional view taken along the line X-X of FIG. 1. As shown in FIGS. 1 and 2, a radiation image capturing device 1 of the embodiment is configured in such a way that a scintillator 3, a substrate 4, and the like is housed in a housing 2.

The housing 2 is made of material which radiation pass through, such as a carbon plate or plastics. At least, a radiation incidence surface R thereof is made of such material. FIGS. 1 and 2 show the housing 2 constituted of a flame plate 2A and a back plate 2B, namely, a housing in a shape of a lunch box. However, the housing 2 can be constituted of one plate to be in a shape of a rectangular cylinder, namely, a monocoque-type housing.

Furthermore, as shown in FIG. 1, a power supply switch 36, an indicator 37 constituted of an LED or the like, a cover 38 which can be opened and closed, for example, to change a not-shown battery 41 (but shown in FIG. 7 described below), and the like are disposed on a lateral surface part of the housing 2. In addition, in the embodiment, an antenna device 39 which is a communication section to communicate with a not-shown external device wirelessly is built in a lateral surface part of the cover 38.

As shown in FIG. 2, a base 31 is disposed under the substrate 4 with a not-shown thin lead plate or the like in between in the housing 2. On the base 31, a PCB substrate 33 provided with electronic components 32 and the like; a cushioning material 34; and the like are mounted. In the embodiment, a glass substrate 35 is disposed on the radiation incidence surface R side of the substrate 4 and the scintillator 3 to protect the substrate 4 and the scintillator 3.

The scintillator 3 is attached to a detection section P (described below) of the substrate 4. The scintillator 3 is, for example, a scintillator which is constituted of a fluorescent substance as a principal constituent, and when radiation enters therein, converts the radiation into electromagnetic waves having a wavelength of 300 nm to 800 nm, namely, electromagnetic waves centering on visible light, and outputs the electromagnetic waves.

Figure 3:
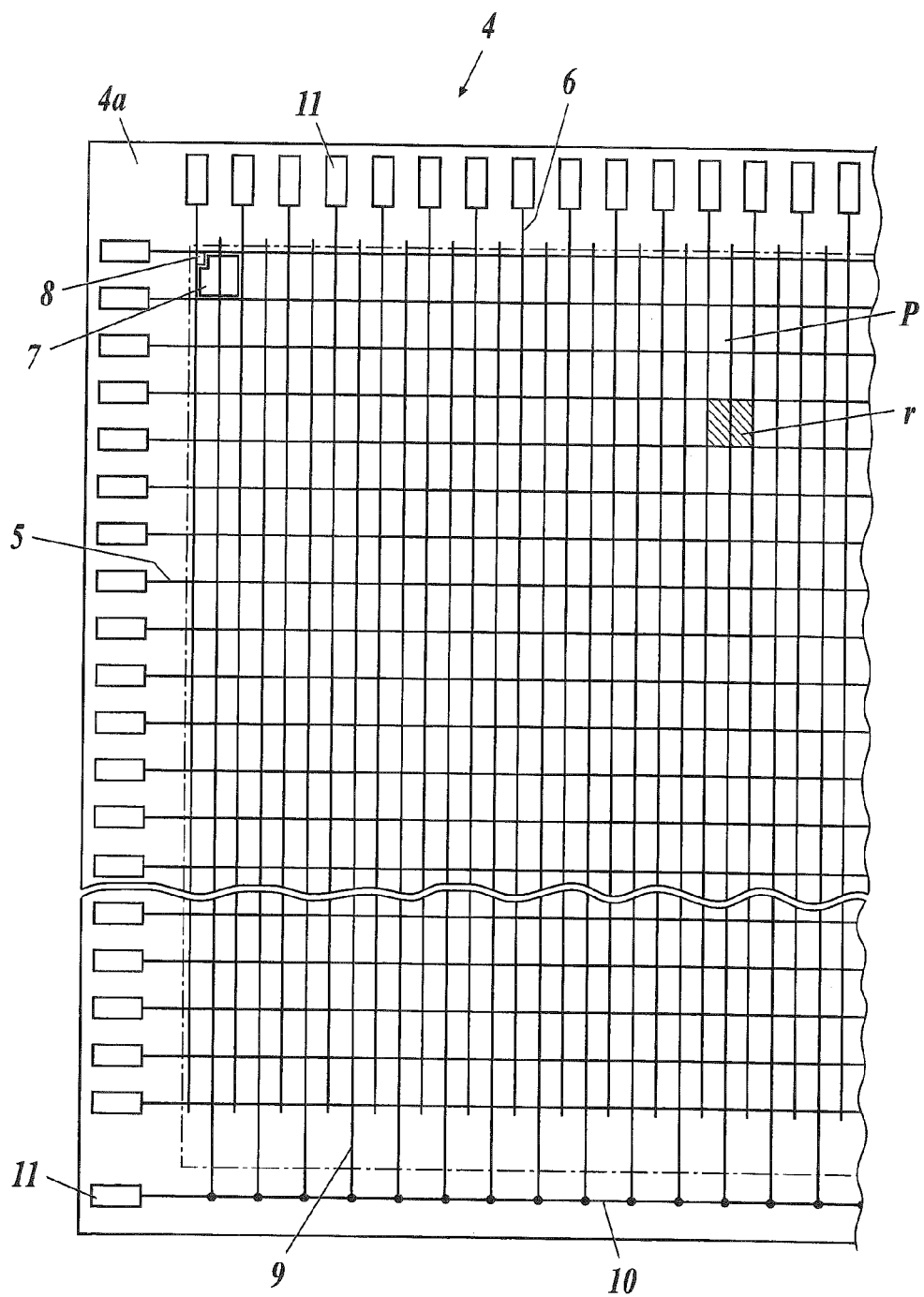
FIG. 3 is a plan view showing the configuration of a substrate of the radiation image capturing device.

The substrate 4 is constituted of a glass substrate in the embodiment. As shown in FIG. 3, on a surface 4a facing the scintillator 3, a plurality of scan lines 5 and a plurality of signal lines 6 are arranged in such a way as to intersect each other. Radiation detection elements 7 are respectively provided in small regions r divided by the scan lines 5 and the signal lines 6 on the surface 4a of the substrate 4.

All the small regions r, which are divided by the scan lines 5 and the signal lines 6, and in which the radiation detection elements 7 are two-dimensionally provided, namely, an area shown in a dash-dot line in FIG. 3, is the detection section P.

Figure 4:
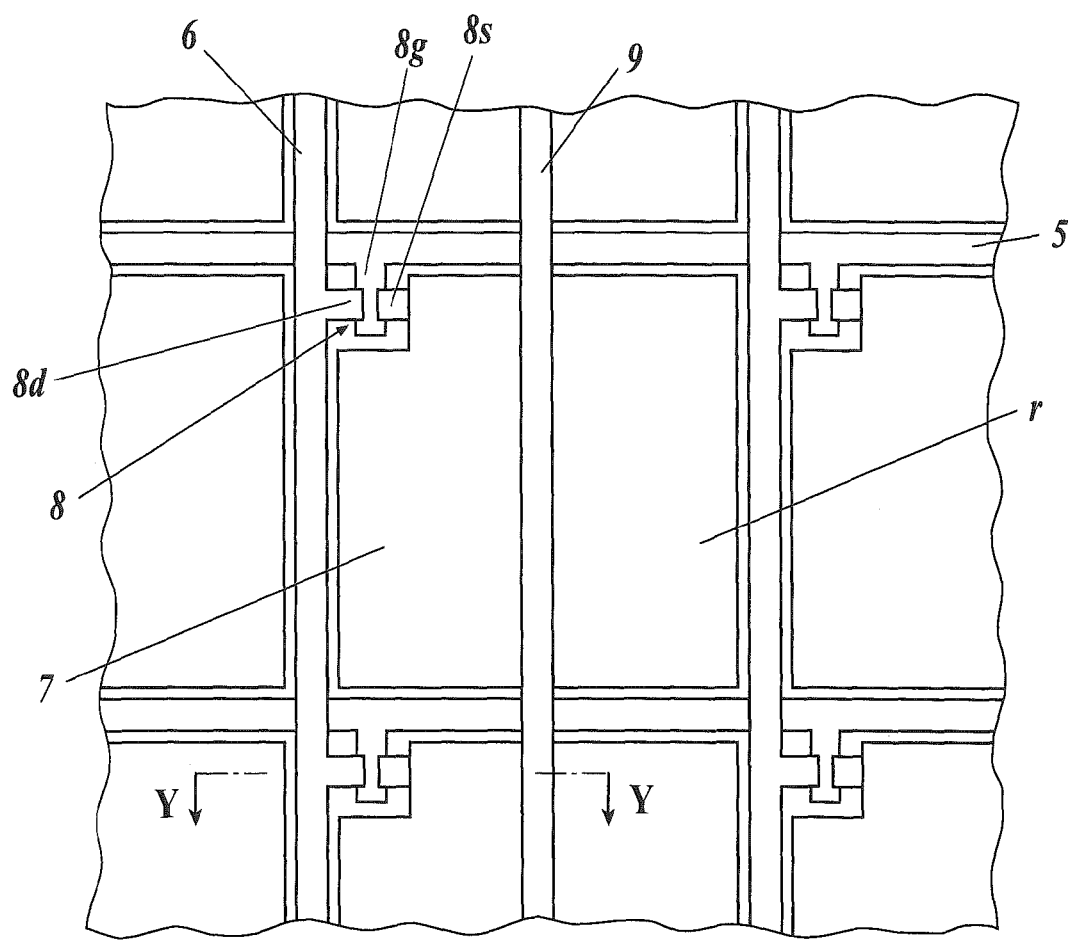
FIG. 4 is an enlarged view showing a radiation detection element, a TFT, and the like formed in a small region on the substrate shown in FIG. 3.

In the embodiment, as the radiation detection elements 7, photo diodes are used. However, for example, photo transistors can be used as the radiation detection elements 7, too. As shown in FIG. 3 and FIG. 4 which is an enlarged view of FIG. 3, each radiation detection element 7 is connected to a source electrode 8s of a TFT 8 which is a switch section. A drain electrode 8d of the TFT 8 is connected to a signal line 6.

The TFT 8 is turned on when an ON-state voltage Von is applied to the connected scan line 5 so as to be applied to a gate electrode 8g. Consequently, the TFT 8 discharges electric charge generated and accumulated in the radiation detection element 7 to the signal line 6. The TFT 8 is turned off when an OFF-state voltage Voff is applied to the connected scan line 5 so as to be applied to the gate electrode 8g. Consequently, the TFT 8 stops discharging the electric charge from the radiation detection element 7 to the signal line 6, and keeps and accumulates the electric charge generated in the radiation detection element 7 therein.

Figure 5:
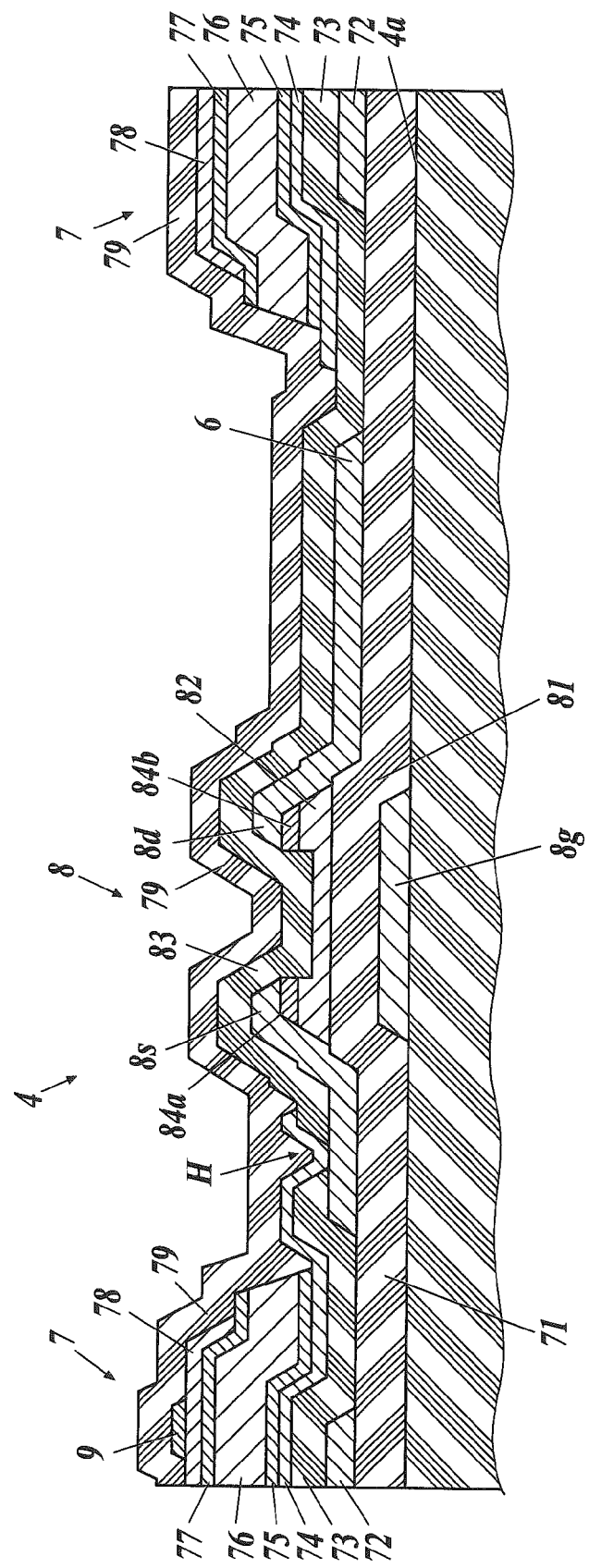
FIG. 5 is a sectional view taken along the line Y-Y of FIG. 4.

The configurations of the radiation detection element 7 and the TFT 8 in the embodiment are briefly described with reference to a sectional view of FIG. 5. FIG. 5 is a sectional view taken along the line Y-Y of FIG. 4.

On the surface 4a of the substrate 4, the gate electrode 8g of the TFT 8 constituted of Al, Cr, or the like is formed. The gate electrode is disposed thereon to be united with the scan line 5. The source electrode 8s connected to a first electrode 74 of the radiation detection element 7 and the drain electrode 8d formed to be united with the signal line 6 are formed by being disposed above a gate insulating layer 81 and the gate electrode 8g, with a semiconductor layer 82 between the gate insulating layer 81 and the source electrode 8s and the drain electrode 8d. The gate insulating layer 81 is constituted of silicon nitride ($SiN_x$) or the like, and disposed on the gate electrode 8g and the surface 4a. The semiconductor layer 82 is constituted of amorphous silicon hydride (a-Si) or the like.

The source electrode 8s and the drain electrode 8d are divided by a first passivation layer 83 constituted of silicon nitride ($SiN_x$) or the like. The first passivation layer 83 covers the electrodes 8s and 8d from above. An ohmic contact layer 84a is disposed between the semiconductor layer 82 and the source electrode 8s. An ohmic contact layer 84b is disposed between the semiconductor layer 82 and the drain electrode 8d. Each of the Ohmic contact layers 84a and 84b is formed by doping amorphous silicon hydride with a VI group element so as to be an n-type. As described above, the TFT 8 is formed.

In the radiation detection element 7, an auxiliary electrode 72 is formed on an insulating layer 71 by Al, Cr, or the like being disposed thereon. The insulating layer 71 is formed to be united with the gate insulating layer 81 on the surface 4a of the substrate 4. The first electrode 74 constituted of AL, Cr, Mo, or the like is disposed on the auxiliary electrode 72 with an insulating layer 73 in between. The insulating layer 73 is formed to be united with the first passivation layer 83. The first electrode 74 is connected to the source electrode 8s of the TFT 8 via a hole H made in the first passivation layer 83.

An n layer 75, an i layer 76, and a p layer 77 are disposed on the first electrode 74 in the order named. The n layer 75 is formed by doping amorphous silicon hydride with a VI group element to be an n-type. The i layer 76 is constituted of amorphous silicon hydride, and is a transforming layer. The p layer 77 is formed by doping amorphous silicon hydride with a III group element to be a p-type.

When radiation enters from the radiation incidence surface R of the housing 2 of the radiation image capturing device 1; the scintillator 3 converts the radiation into the electromagnetic waves such as visible light; and the electromagnetic waves are emitted from the above in FIG. 5, the electromagnetic waves reach the i layer 76 of the radiation detection element 7, and an electron-hole pair is generated in the i layer 76. Thus, the radiation detection element 7 converts the electromagnetic waves emitted from the scintillator 3, into electric charge.

On the p layer 77, a second electrode 78 of a transparent electrode such as an ITO is disposed and formed, so that the electromagnetic waves reach the i layer 76 and the like. In the embodiment, as described above, the radiation detection element 7 is formed. The n layer 75, the i layer 76, and the p layer 77 may be disposed in the order opposite to the order described above. In the embodiment, as the radiation detection element 7, the so-called pin-type radiation detection element is used. The pin-type radiation detection element is formed, as described above, by the n layer 75, the i layer 76 and the p layer 77 being disposed in the order named. However, this is not a limit.

To the upper surface of the second electrode 78 of the radiation detection element 7, a bias line 9 which applies a bias voltage to the radiation detection element 7 via the second electrode 78 is connected. The second electrode 78, the bias line 9 in the radiation detection element 7, the first electrode 74 extending to the TFT 8 side, the first passivation layer 83, and the like, namely the upper surface parts of the radiation detection element 7 and the TFT 8, are covered with a second passivation layer 79 constituted of silicon nitride ($SiN_x$) or the like from the above.

As shown in FIGS. 3 and 4, in the embodiment, each bias line 9 is connected to a plurality of radiation detection elements 7 arranged in a column. The bias lines 9 are arranged parallel to the signal lines 6. The bias lines 9 are bound with a connection line 10 outside of the detection section P of the substrate 4.

Figure 6:
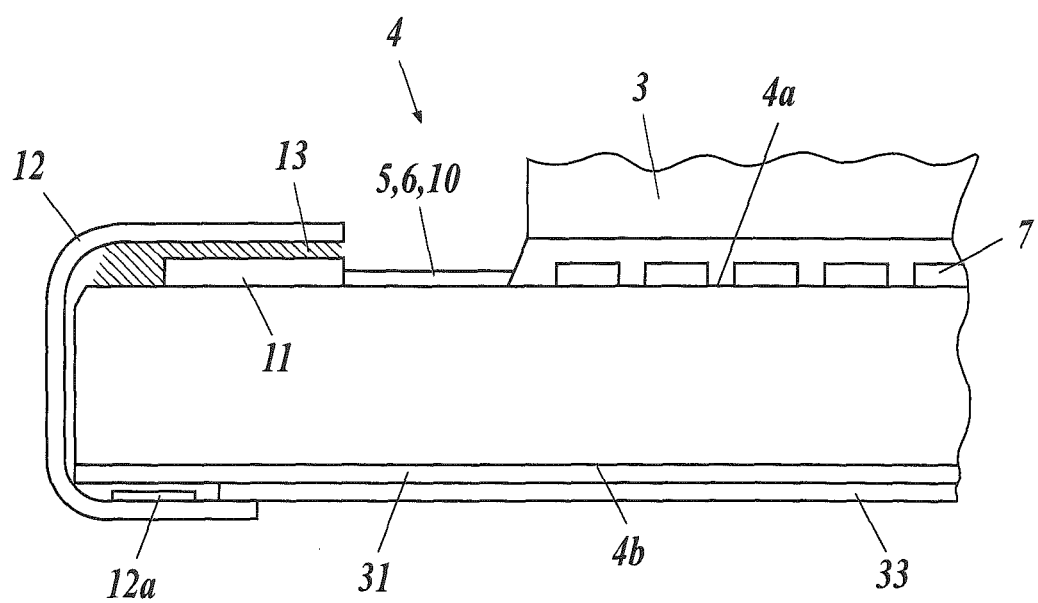

In the embodiment, as shown in FIG. 3, the scan lines 5, the signal lines 6, and the connection line 10 for the bias lines 9 are connected to input/output terminals (also called as pads) 11, respectively. Each of the input/output terminals 11 is, as shown in FIG. 6, provided near the edge part of the substrate 4. A COF (Chip On Film) 12 in which a chip such as a gate IC 12a constituting a gate driver 15b of a scan driving section 15 (described below) is built is connected to each input/output terminal 11 through an anisotropic conductive adhesive material 13 such as an anisotropic conductive film or an anisotropic conductive paste.

The COF 12 is pulled to a back surface 4b side of the substrate 4, and connected to the above-described PCB substrate 33 on the back surface 4b side. Thus, the substrate 4 of the radiation image capturing device 1 is formed. In FIG. 6, the electronic components 32 and the like are not shown.

Figure 7:
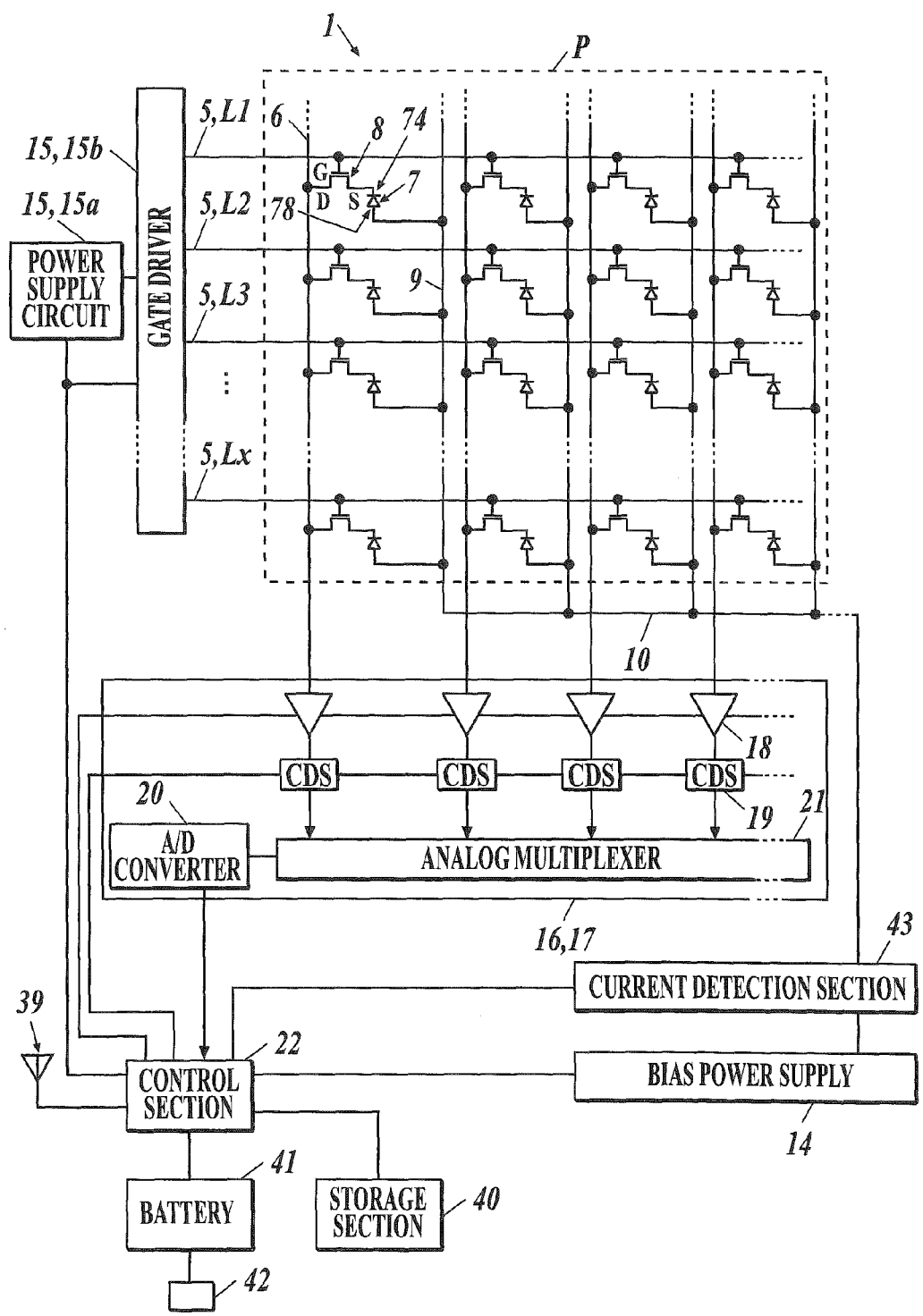
FIG. 7 is a block diagram showing an equivalent circuit of the radiation image capturing device.
Figure 8:
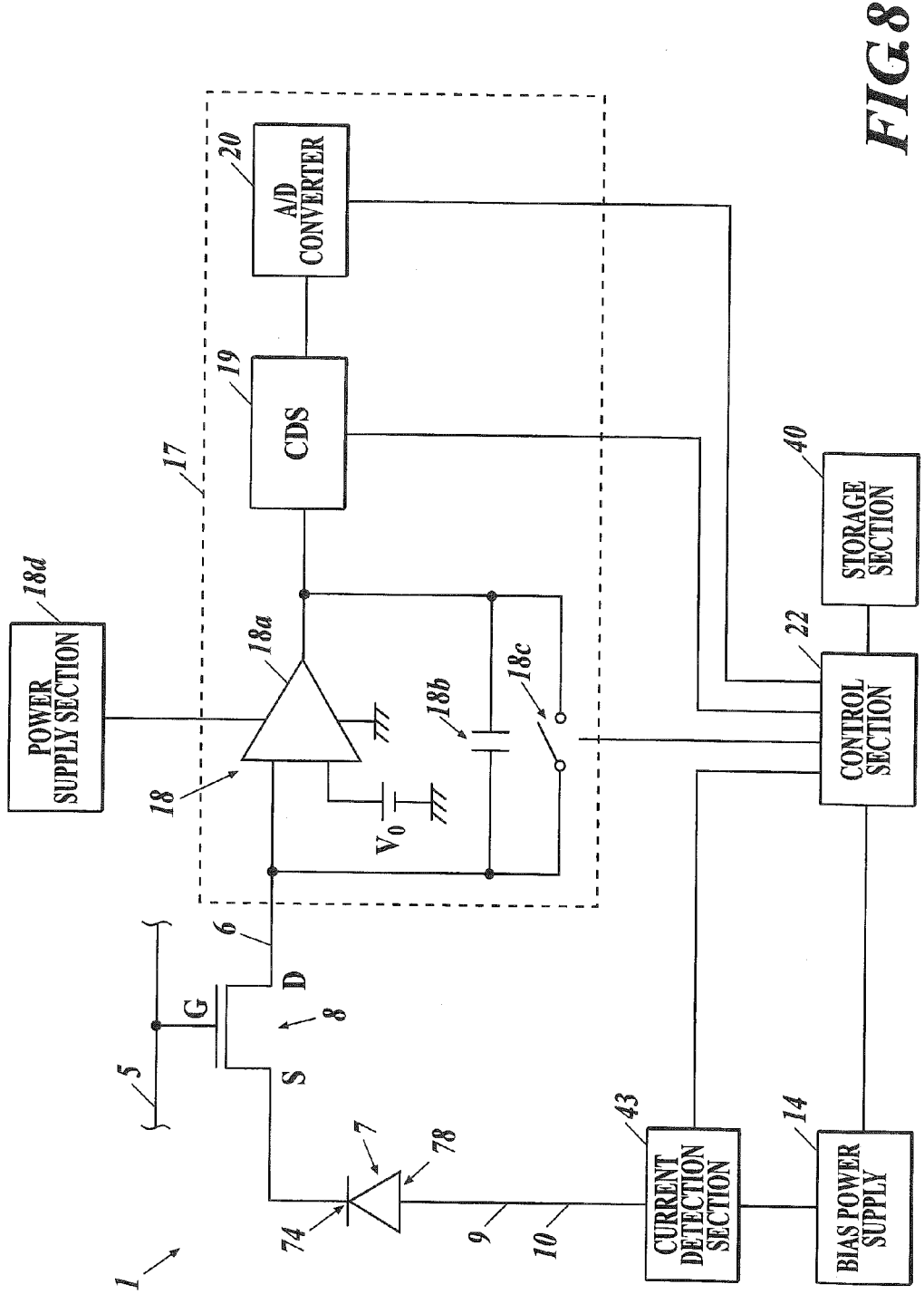
FIG. 8 is a block diagram showing an equivalent circuit of one pixel of a detection section.

Here, the circuit configuration of the radiation image capturing device 1 is described. FIG. 7 is a block diagram showing an equivalent circuit of the radiation image capturing device 1 of the embodiment. FIG. 8 is a block diagram showing an equivalent circuit of one pixel of the detection section P.

As described above, in each radiation detection element 7 of the detection section P of the substrate 4, a bias line 9 is connected to the second electrode 78, and a plurality of bias lines 9 are bound with the connection line 10 so as to be connected to a bias power supply 14. The bias power supply 14 applies a bias voltage to the second electrodes 78 of the radiation detection elements 7 via the connection line 10 and the bias lines 9. Furthermore, the bias power supply 14 is connected to a control section 22 (described below). The control section 22 controls the bias voltage applied to the radiation detection elements 7 from the bias power supply 14.

In the embodiment, the connection line 10 for the bias lines 9 is provided with a current detection section 43 which detects the amount of current flowing in the connection line 10 (bias lines 9). The current detection section 43 detects the increase and the decrease of the current flowing in the connection line 10, and consequently, detects the start and the end of the irradiation.

FIGS. 7 and 8 and also FIG. 3 and the like described above show that a plurality of bias lines 9 is bound with one connection line 10. In this case, it is possible to provide one connection line 10 with one current detection section 43. However, there is a case where a plurality of bias lines 9 is bound with a plurality of connection lines 10. In such a case, each connection line 10 may be provided with a current detection section 43. Alternatively, each of some of connection lines 10 may be provided with a current detection section 43.

In the embodiment, the current detection section 43 is provided for the bias lines 9 and the connection line 10, and detects the current flowing in the bias lines 9 and the connection line 10 owing to the irradiation to the radiation image capturing device 1. However, as long as the current detection section 43 can detect the current flowing in the radiation image capturing device 1 owing to the irradiation thereto, it is not necessary to provide the bias lines 9 and the connection line 10 with the current detection section 43.

Here, the configuration of the current detection section 43 is described. In the embodiment, the current detection section 43 is set up at a connection part of the connection line 10 for the bias lines 9 and the bias power supply 14, and detects the current flowing between the bias power supply 14 and the radiation detection elements 7 in response to the start of the irradiation.

Figure 9:
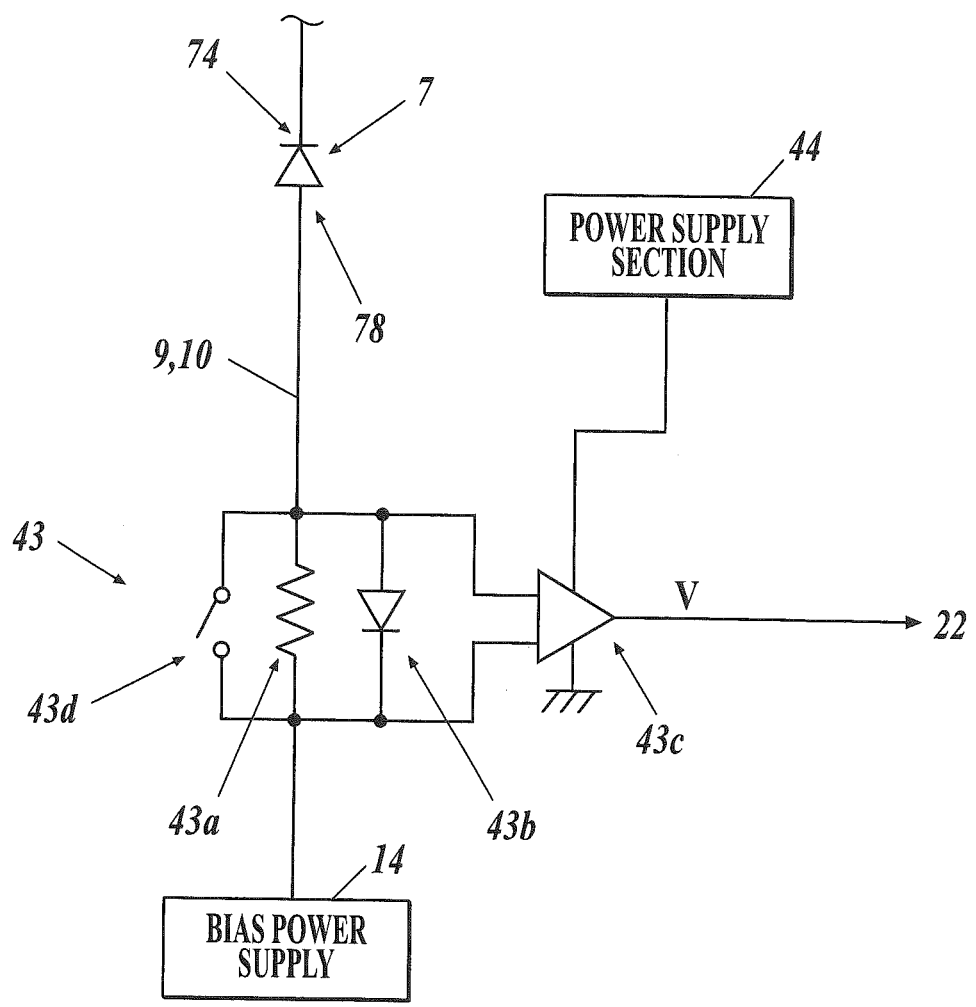
FIG. 9 is an equivalent circuit diagram showing the configuration of a current detection section.

More specifically, as shown in FIG. 9, the current detection section 43 includes a resistor 43a, a diode 43b, and a differential amplifier 43c. The resistor 43a has a predetermined resistance value and is connected to the connection line 10 for the bias lines 9 in series, the connection line 10 connecting the bias power supply 14 and the radiation detection elements 7. The diode 43b is connected parallel to the resistor 43a. The differential amplifier 43c measures a voltage V between both terminals of the resistor 43a, and outputs the measured voltage V to the control section 22.

Thus, in the embodiment, the current detection section 43, with the differential amplifier 43c, measures the voltage V between both terminals of the resistor 43a, converts the current flowing in the resistor 43a, namely, the current flowing in the connection line 10 for the bias lines 9, into the voltage value V and detects the voltage value V, and outputs the voltage value V to the control section 22.

As the resistor 43a of the current detection section 43, a resistor having a resistance value with which the current flowing in the connection line 10 can be converted into an appropriate voltage value V is used. By connecting the diode 43b parallel to the resistor 43a, the detection accuracy in the case of a low dose of radiation is increased. It is possible to connect only one of the resistor 43a and the diode 43b to the connection line 10 in series, and measure the voltage V between the terminals of the resistor 43a or the diode 43b with the differential amplifier 43c.

Except for the case where the start or the end of the irradiation is detected, it is unnecessary to detect the current flowing between the bias power supply 14 and the radiation detection elements 7 with the current detection section 43. Then, the resistor 43a of the current detection section 43 is an obstacle to apply the bias voltage from the bias power supply 14 to the radiation detection elements 7. Hence, the current detection section 43 is provided with a switch 43d to short-circuit the terminals of the resistor 43a as needed when the detection of a current is unnecessary.

Power is supplied to the differential amplifier 43c from a power supply section 44. When the current detection section 43 detects a current, the power supply section 44 supplies power to the differential amplifier 43c, and the short circuit made by the switch 43d is cancelled so that the current detection section 43 operates. When it is unnecessary that the current detection section 43 detects a current, the switch 43d short-circuits the terminals of the resistor 43a, and the power supply section 44 stops supplying power to the differential amplifier 43c so that the current detection section 43 stops operating.

As shown in FIGS. 7 and 8, in the embodiment, the bias line 9 is connected onto the p layer 77 (shown in FIG. 5) of the radiation detection element 7 via the second electrode 78, from which it is known that the bias power supply 14 applies a voltage as a bias voltage to the second electrode 78 of the radiation detection element 7 via the bias line 9, the voltage being equal to or less than a voltage applied to the first electrode 74 of the radiation detection element 7, namely the so-called reverse bias voltage.

The first electrode 74 of each radiation detection element 7 is connected to the source electrode 8s (represented by "S" in FIGS. 7 and 8) of a TFT 8. The gate electrode 8g (represented by "G" in FIGS. 7 and 8) of each TFT 8 is connected to one of the lines L1 to Lx of the scan lines 5 extending from the gate driver 15b of the scan driving section 15 (described below). The drain electrode 8d (represented by "D" in FIGS. 7 and 8) of each TFT 8 is connected to one of the signal lines 6.

In the embodiment, the scan driving section 15 includes a power supply circuit 15a and the gate driver 15b. In the embodiment, the gate driver 15b is constituted of a plurality of gate ICs 12a (described above) being arranged parallel to each other. The scan driving section 15 controls a voltage applied to the gate electrodes 8g of the TFTs 8 via the lines L1 to Lx of the scan lines 5 connected to the gate driver 15b, and switches the voltage between the above-described ON-state voltage Von and OFF-state voltage Voff.

More specifically, the power supply circuit 15a of the scan driving circuit 15 sets the values of the ON-state voltage Von and the OFF-state voltage Voff applied to the scan lines 5 from the gate driver 15b at predetermined voltage values, respectively, and supplies the voltage values of the voltages to the gate driver 15b. Furthermore, the gate driver 15b of the scan driving section 15 selectively switches between the ON-state voltage Von and the OFF-state voltage Voff both supplied from the power supply circuit 15a so as to apply the ON-state voltage Von or the OFF-state voltage Voff to the lines L1 to Lx of the scan lines 5. Moreover, the gate driver 15b can modulate the pulse width of the ON-state voltage Von of a pulse shape, the ON-state voltage Von being applied to the lines L1 to Lx of the scan lines 5.

In the embodiment, the power supply circuit 15a of the scan driving section 15 has a function to adjust the voltage value of the ON-state voltage Von applied to the gate electrodes 8g of the TFTs 8 via the lines L1 to Lx of the scan lines 5. As described below, in reset processing of the radiation detection elements 7 performed before the radiation image capturing, first, the ON-state voltage Von, which is applied to the gate electrodes 8g of the TFTs 8 at the time of reading image data from the radiation detection elements 7, namely, the ON-state voltage Von having the highest voltage value, is applied to the gate electrodes 8g of the TFTs 8 all at once, and then, the voltage value of the ON-state voltage Von is decreased all at once.

In the following, the ON-state voltage Von which is as high as the voltage applied to the gate electrodes 8g of the TFTs 8 first in the reading of image data from the radiation detection elements 7 is expressed by "Von1". The ON-state voltage Von which is decreased thereafter is expressed by "Von2". The ON-state voltage Von in general is expressed by "Von".

In the embodiment, as described above, the power supply circuit 15a of the scan driving section 15 is configured to have the function to adjust the voltage value of the ON-state voltage Von. However, a component which has the function to adjust the voltage value of the ON-state voltage Von may be provided separately from the power supply circuit 15a.

The signal lines 6 are connected to reading circuits 17 formed in reading ICs 16. Each of the reading IC 16 includes a predetermined number of reading circuits 17. By providing a plurality of reading ICs 16, the reading circuits 17 for the number of signal lines 6 are provided.

A reading circuit 17 includes an amplifier circuit 18, a correlated double sampling circuit 19, an analog multiplexer 21, and an A/D converter 20. In FIGS. 7 and 8 and also in FIG. 10 described below, the correlated double sampling circuit 19 is represented by "CDS". In FIG. 8, the analog multiplexer 21 is not shown.

In the embodiment, the amplifier circuit 18 is constituted of a charge amplifier circuit, and includes an operational amplifier 18a, and a capacitor 18b and a charge-reset-use switch 18c both connected to the operational amplifier 18a parallel. A power supply section 18d for supplying power to the amplifier circuit 18 is connected to the amplifier circuit 18.

The signal line 6 is connected to a reverse input terminal on the input side of the operational amplifier 18a of the amplifier circuit 18, and a reference potential $V_0$ is applied to a non-reverse input terminal on the input side of the amplifier circuit 18. The reference potential $V_0$ is set at an appropriate value. In the embodiment, 0[V] is applied to the non-reverse input terminal as the reference potential $V_0$.

The charge-reset-use switch 18c of the amplifier circuit 18 is connected to the control section 22 described below, and the control section 22 controls on/off of the switch 18c. In the reading processing of image data from the radiation detection elements 7, when the charge-reset-use switch 18d is off and the TFTs 8 of the radiation detection elements 7 are turned on (namely, when the ON-state voltage Von 1 for reading signals is applied to the gate electrodes 8g of the TFTs 8 via the scan lines 5), electric charge discharged from the radiation detection elements 7 flows into the capacitor 18b and is accumulated therein. Then, a voltage value in accordance with the accumulated amount of electric charge is outputted from the output side of the operational amplifier 18a.

Thus, the amplifier circuit 18 outputs a voltage value in accordance with the charge amount outputted from the radiation detection elements 7, and performs the amplification by the charge-voltage conversion. Furthermore, when the charge-reset-use switch 18c is turned on, the input side and the output side of the amplifier circuit 18 are short-circuited, the charge accumulated in the capacitor 18b is discharged, and hence the amplifier circuit 18 is reset. The amplifier circuit 18 may be configured to output a current in accordance with charge outputted from the radiation detection elements 7.

The correlated double sampling circuit 19 is connected to the output side of the amplifier circuit 18. In the embodiment, the correlated double sampling circuit 19 has a sample holding function. By pulse signals transmitted from the control section 22, on/off of the sample holding function of the correlated double sampling circuit 19 is controlled.

That is, in the reading processing of image data from the radiation detection elements 7 after the radiation image capturing, the control section 22 first controls the charge-reset-use switches 18c of the amplifier circuits 18 of each reading circuit 17 to turn them off. At the moment when the charge-reset-use switches 18c are turned off, the so-called kTC noise is generated, and charge q resulted from the kTC noise is accumulated in the capacitors 18b of the amplifier circuits 18.

As described above, in each amplifier circuit 18, the voltage value in accordance with the charge amount accumulated in the capacitor 18b is outputted from the output terminal of the operational amplifier 18a of the amplifier circuit 18. However, by the charge q resulted from the kTC noise being accumulated in the capacitor 18b, as shown in FIG. 10, the voltage value outputted from the output terminal of the operational amplifier 18a changes for the charge q resulted from the kTC noise, namely, from the above-described reference potential $V_0$ to a voltage value Vin, at the moment when the charge-reset-use switch 18c is turned off (represented by "18coff" in FIG. 10).

The control section 22 transmits the first pulse signal Sp1 to the correlated double sampling circuit 19 at this point of time (represented by "ODS KEEP" on the left in FIG. 10), and makes the correlated double sampling circuit 19 keep the voltage value Vin which is outputted from the amplifier circuit 18 at the time.

Next, when the control section 22 applies the ON-state voltage Von1 to one scan line 5 from the scan driving circuit 15, and accordingly turns on the TFTs 8 each having the gate electrode 8g connected to the scan line 5 (represented by "TFTon" in FIG. 10), the charge accumulated in the radiation detection elements 7 connected to the TFTs 8 flows into the capacitors 18b of the amplifier circuits 18 via the signal lines 6, and are accumulated therein. Then, as shown in FIG. 10, the voltage value outputted from the output side of each of the operational amplifiers 18a increases in accordance with the charge amount accumulated in the capacitors 18b.

Figure 10:
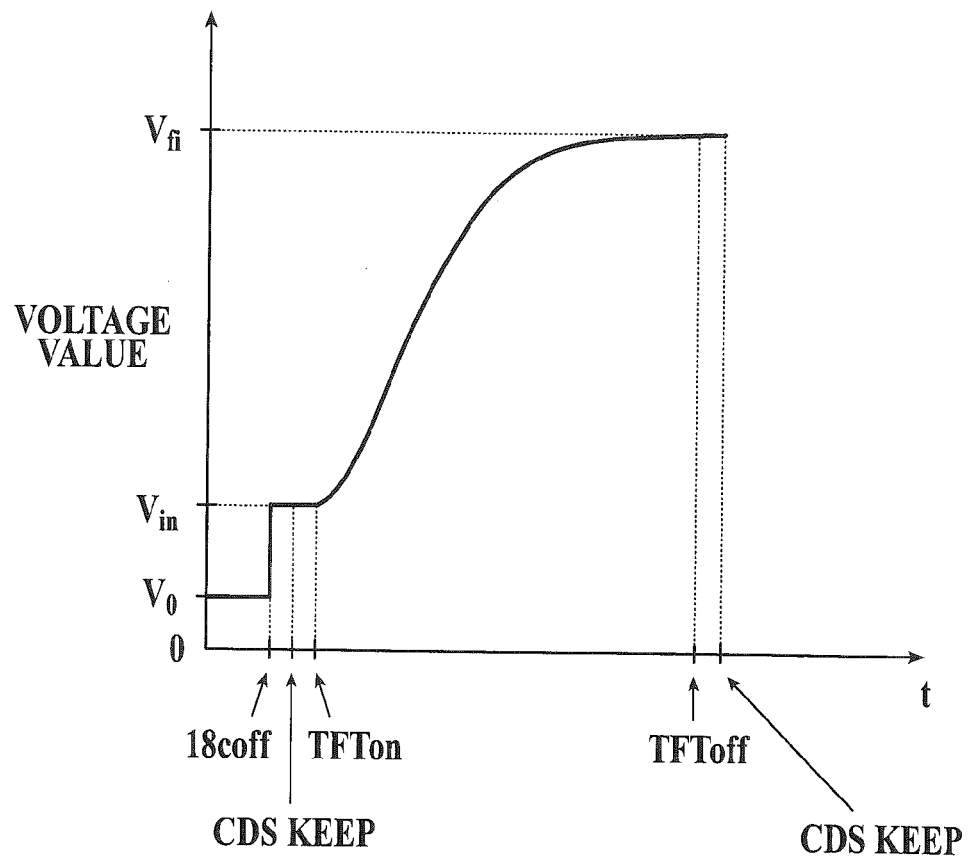
FIG. 10 is a graph showing change of a voltage value and the like in a correlated double sampling circuit.

After a predetermined time elapses, the control section 22 switches the ON-state voltage Von1 applied to the scan line 5 from the scan driving circuit 15 to the OFF-state voltage Voff, and accordingly turns off the TFTs 8 each having the gate electrode 8g connected to the scan line 5 (represented by "TFToff" in FIG. 10). The control section 22 transmits the second pulse signal Sp2 to the correlated double sampling circuits 19 at this point of time (represented by "ODS KEEP" on the right in FIG. 10), and makes the correlated double sampling circuits 19 keep the voltage Vfi which is outputted from the amplifier circuits 18 at this point of time (represented by "ODS KEEP" on the right in FIG. 10).

While keeping the voltage value Vfi in accordance with the second pulse signal Sp2, each of the correlated double sampling circuits 19 calculates a difference Vfi−Vin between the voltage values Vfi and Vin, and outputs the calculated difference Vfi−Vin as the image data to the downstream side.

The image data of each of the radiation detection elements 7 outputted from each of the correlated double sampling circuits 19 is transmitted to the analog multiplexers 21 (shown in FIG. 7), and then to the A/D converters 20 consecutively. Then, the image data is converted into image data of digital values consecutively by the A/D converters 20, outputted to the storage section 40, and stored therein consecutively.

The control section 22 is constituted of a computer in which a not-shown CPU (Central Processing Unit), a ROM (Read Only Memory), a RAM (Random Access Memory), an input/output interface, and the like are connected by a bus; a FPGA (Field Programmable Gate Array); or the like. The control section 22 may be constituted of a control circuit for exclusive use. The control section 22 controls the operations and the like of the components of the radiation image capturing device 1. Furthermore, the storage section 40 constituted of a DRAM (Dynamic RAM) or the like is connected to the control section 22.

In the embodiment, the above-described antenna device 39 is connected to the control section 22. Furthermore, a battery 41 is connected to the control section 22. The battery 41 supplies power to the components, such as the detection section P, the scan driving section 15, the reading circuit 17, the storage section 40, and the bias power supply 14. A connection terminal 42 is installed in the battery 41. The connection terminal 42 is used when the battery 41 is charged by an external device which supplies power to the battery 41.

As described above, the control section 22 performs various types of processing. For example, the control section 22 controls the bias power supply 14 to set a bias voltage applied to the radiation detection elements 7 from the bias power supply 14, controls on/off of the charge-reset-use switches 18c of the amplifier circuits 18 of the reading circuits 17, and transmits pulse signals to the correlated double sampling circuits 19 to control on/off of the sample holding functions of the correlated double sampling circuits 19.

Furthermore, in the reset processing of the radiation detection elements 7 and the reading of image data from the radiation detection elements 7 after the radiation image capturing, the control section 22 transmits pulse signals to the scan driving section 15. The pulse signal are signals to switch the voltage, which is applied to the gate electrode 8g of each TFT 8 via each scan line 5 from the scan driving section 15, between the ON-state voltage Von and the OFF-state voltage Voff.

In the following, the control configuration of the control section 22 and the operation of the radiation image capturing device 1 in the reset processing of the radiation detection elements 7 and the like are described.

As shown in FIGS. 23A, 23B, 24A and 24B, in conventional reset processing of the radiation detection elements 7, when radiation detection elements 7 in a region R1 is exposed to strong radiation by being exposed to the radiation not passing through a subject or the like, image data having a significant value, namely, not "0", is generated in radiation detection elements 7 in regions R2 or a region Rh each adjacent to the region R1, owing to the radiation detection elements 7 in the region R1. The reason therefor is explained.

Figure 23A:
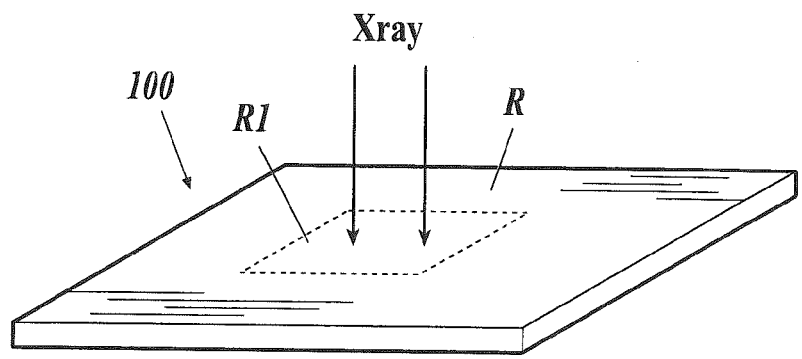
FIG. 23A shows a strongly-irradiated region.
Figure 23B:
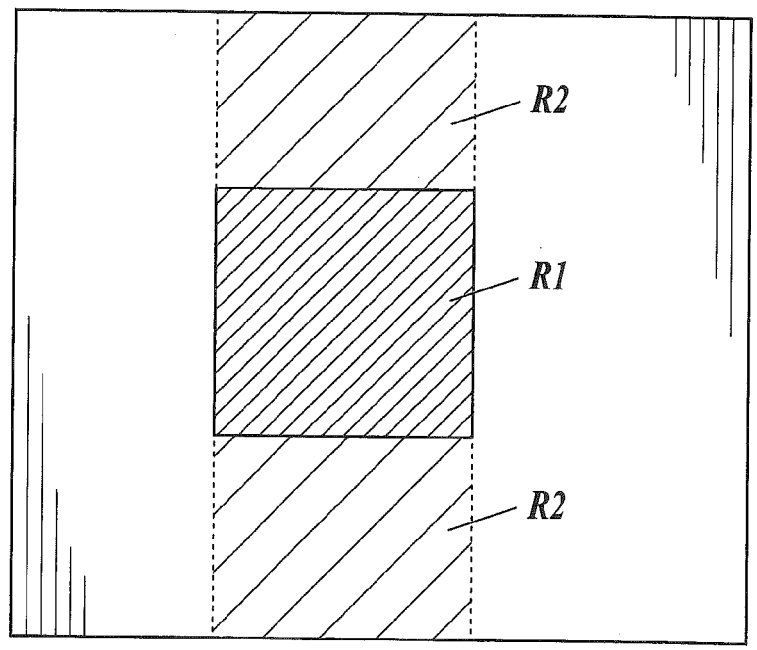
FIG. 23B shows a non-irradiated region adjacent to the region shown in FIG. 23A, and captured somewhat in black.

For example, as shown in FIG. 23, in the regions R2 adjacent to the region R1 in the up-down direction, the region R1 exposed to the strong radiation, image data having a significant value is generated. However, in regions adjacent to the region R1 in the right-left direction, image data having a significant value is not generated owing to the radiation detection elements 7 in the region R1. Note that, in this case, although not being shown in FIG. 23B, signal lines 6 are arranged to extend in the up-down direction in FIG. 23B.

Therefore, the cause which generates image data having a significant value in the radiation detection elements 7 of the regions R2 or the like is considered as follows.

That is, in the reset processing of the radiation detection elements 7 performed before the radiation image capturing, the ON-state voltage Von1 is applied to the gate electrode 8g of each TFT 8, and the gate of each TFT 8 is opened to discharge the excess charge such as dark charge accumulated in each radiation detection element 7. Then, as described above, each TFT 8 waits with the ON-state voltage Von1 applied to the gate electrode 8g. When irradiation starts, electron-hole pairs are generated in the radiation detection elements 7. The electron-hole pairs start to flow into the bias lines 9 and the connection line 10. Consequently, the increase of the value of the current flowing in the bias lines 9 or the like is detected, and accordingly, the start of the irradiation is detected.

Here, explanation is made with reference to the equivalent circuit of FIG. 8. When the electron-hole pairs are generated in the radiation detection elements 7 by irradiation, the holes start to flow from the second electrode 78 side of the radiation detection elements 7 to the bias lines 9 and the connection line 10, and flow into the bias power supply 14 via the current detection section 43. In addition, the electrons start to flow from the first electrode 74 side of the radiation detection elements 7 to the signal lines 6 via the TFTs 8, flow through the signal lines 6, and flow out to the downstream side of the reading circuits 17 and the like.

Originally, to the second electrodes 78 of the radiation detection elements 7, the bias voltage (in the embodiment, the reverse bias voltage) Vbias is applied from the bias power supply 14 via the bias lines 9. However, when the holes flowing from the second electrodes 78 flow in the bias lines 9 or the current detection section 43, because the bias lines 9 themselves and the resistor 43a and the diode 43b of the current detection section 43 have resistance, a voltage difference is generated with a relation of V=IR. Consequently, the bias voltage Vbias applied to the second electrodes 78 of the radiation detection elements 7 from the bias power supply 14 fluctuates.

Similarly, as described above, originally, to the first electrodes 74 of the radiation detection elements 7, the reference potential $V_0$ is applied from the amplifier circuits 18 of the reading circuits 17 via the signal lines 6. However, when the electrons flowing from the first electrodes 74 flow in the signal lines 6 or the reading circuits 17, because the signal lines 6 themselves and the reading circuits 17 have resistance, again, a voltage difference is generated with a relation of V=IR. Consequently, the reference potential $V_0$ applied to the first electrodes 74 of the radiation detection elements 7 from the amplifier circuits 18 fluctuates.

As shown in FIG. 7, the first electrodes 74 of a plurality of radiation detection elements 7 are connected to one signal line 6 via a plurality of TFTs 8, and the second electrodes 78 of the radiation detection elements 7 are connected to one bias line 9.

Consequently, when some of the radiation detection elements 7 connected to the one signal line 6 discharge electrons and holes by being irradiated, and as described above, the voltage fluctuation at the signal line 6 and the bias line 9 occurs thereby, the reference potential $V_0$ applied to the first electrodes 74 and the bias voltage Vbias applied to the second electrodes 78 fluctuate in the radiation detection elements 7 each of which has the first electrode 74 and the second electrode 78 connected to the signal line 6 and the bias line 9, but which is not irradiated.

Therefore, the non-irradiated radiation detection elements 7 become in a state in which as if charge is generated therein in accordance with the voltage fluctuation at the signal line 6 and the bias line 9 with a relation of Q=CV.

As described above, when the TFTs 8 are kept on, the charge (image data) generated in the radiation detection elements 7 by irradiation is discharged from the radiation detection elements 7. Hence, the voltage applied to the gate electrodes 8g of the TFTs 8 is switched to the OFF-state voltage Voff to switch to a charge-accumulation mode in which the charge (image data) is accumulated. However, regardless of the non-irradiated radiation detection elements 7, the charge generated by the voltage fluctuation at the signal line 6 and the bias line 9 is accumulated in the above-described non-irradiated radiation detection elements 7 by the TFTs 8 being turned off.

Therefore, it is thought that in the reading processing of image data performed thereafter, when charge (image data) is read from the radiation detection elements 7, as shown in FIG. 23B, image data having a significant value, namely, not "0", is read from the radiation detection elements 7 in the regions R2 adjacent to the region R1 of the strongly-irradiated radiation detection elements 7, which are strongly irradiated. That is, image having a significant value is read from the non-irradiated radiation detection elements 7 connected to the same signal line 6 and bias line 9 as the strongly-irradiated radiation detection elements 7, too.

This is known from the fact that even when radiation detection elements 7 are in a region adjacent to a region of the strongly-irradiated radiation detection elements 7, like the regions adjacent to the region R1 in the right-left direction in FIG. 23B, image data having a significant value is not read from non-radiation detection elements 7 connected to a signal line 6 and a bias line 9 different from the signal line 6 and the bias line 9 to which the strongly-irradiated radiation detection elements 7 are connected.

In the embodiment, in order to prevent such a phenomenon from occurring, and to increase the reset efficiency in the reset processing of the radiation detection elements 7, in the reset processing of the radiation detection elements 7 performed before the radiation image capturing, as described above, the control section 10 first applies the ON-state voltage Von1 having a predetermined voltage value (namely, the ON-state voltage having a high voltage value equal to the voltage value of the ON-state voltage Von applied to the gate electrodes 8g of the TFTs 8 in the reading processing of image data, in the embodiment) to the gate electrodes 8g of the TFTs 8 all at once, and then decreases the voltage value of the ON-state voltage Von to apply the ON-state voltage Von2 having a lower voltage value than the voltage value of the ON-state voltage Von1 to the gate electrodes 8g of TFTs 8 from the scan driving section 15 (shown in FIG. 7) via the lines L1 to Lx of the scan lines 5.

Figure 11:
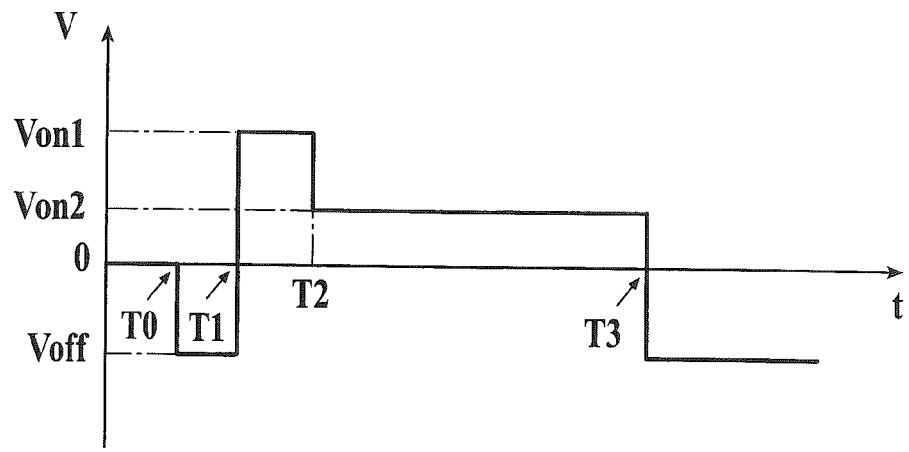
FIG. 11 is a timing chart in reset processing performed before radiation image capturing according to a first embodiment and a second embodiment of the present invention.

More specifically, for example, when the power supply switch 36 of the radiation image capturing device 1 is pressed to start the radiation image capturing device 1, or when a signal to start the reset processing of the radiation detection elements 7 is received via the antenna device 39, as shown in FIG. 11 as an example, the control section 22 applies the OFF-state voltage Voff having a predetermined voltage value (−10[V], for example) to the lines L1 to Lx of the scan lines 5 from the scan driving section 15 all at once so as to turn off the TFTs 8 (time T0).

Furthermore, the control section 22 starts the reading circuits 17 and the like, and transmits a signal to the bias power supply 14 to apply the bias voltage Vbias having a predetermined voltage value (−5[V], for example) to the radiation detection elements 7 from the bias power supply 14 via the bias lines 9 and the connection line 10.

Next, the control section 22 applies, all at once, to the gate electrodes 8g of the TFTs 8, a normal voltage, namely, in the embodiment, the ON-state voltage Von1 having a high voltage value (+15[V], for example) equal to the voltage value of the ON-state voltage Von applied to the gate electrodes 8g of the TFTs 8 in the reading processing of image data.

Thus, by applying the ON-state voltage Von1 having a high voltage value to the gate electrodes 8g of the TFTs 8 at the beginning of the reset processing of the radiation detection elements 7, the excess charge such as dark charge accumulated in the radiation detection elements 7 is certainly discharged therefrom. Accordingly, the reset efficiency of the reset processing of the radiation detection elements 7 can be increased.

In the embodiment, in order to prevent the above-described phenomenon from occurring, at a time T2 by which a predetermined time elapses after the control section 22 applies the ON-state voltage Von1 having a high voltage value to the gate electrodes 8g of the TFTs 8, the control section 22 decreases the ON-state voltage Von applied to the gate electrodes 8g of the TFTs 8 from the ON-state voltage Von1 to the ON-state voltage Von2 having a lower voltage value than the voltage value of the ON-state voltage Von1 all at once, and keeps the ON-state voltage Von2.

In the embodiment, the predetermined time (i.e. T2-T1) is preset by performing experiments or the like in advance, as a time long enough to certainly discharge the excess charge from the radiation detection elements 7. However, for example, it is possible to start the current detection section 43 at the time T1, monitor the current value (or the voltage value V corresponding thereto) outputted from the current detection section 43, and switch the ON-state voltage Von applied to the gate electrodes 8g of the TFTs 8 to the ON-state voltage Von2 having a lower voltage value at the time when the voltage value decreases down to a voltage value indicating that the excess charge are sufficiently discharged from the radiation detection elements 7.

Furthermore, in the embodiment, the voltage value of the ON-state voltage Von2, the voltage value being low, is set at a voltage value with which when the ON-state voltage Von2 is applied to the gate electrodes 8g of the TFTs 8 to turn on the TFTs 8, the maximum current amount i max (Von2) of an ON-state current flowing in the TFTs 8 becomes a little more than a current amount i leak of a leak current including a dark current flowing in the radiation detection elements 7.

That is, when the ON-state voltage having the voltage value Von is applied to the gate electrodes 8g of the TFTs 8 to turn on the TFTs 8, the maximum current amount i max (Von) of the ON-state current flowing in the TFTs 8 changes depending on the voltage value of the ON-state voltage Von applied to the gate electrodes 8g of the TFTs 8. Therefore, the smaller the voltage value Von of the ON-state voltage becomes, the smaller the maximum current value i max (Von) of the ON-state current flowing in the TFTs 8 becomes. When the voltage value Von of the ON-state voltage becomes small enough to reach a threshold value Vth, the current amount possible to flow in the TFTs 8 rapidly decreases.

The rapidly-decreased current amount possible to flow in the TFTs 8 is around four to five digits smaller in value than the current amount of the ON-state current, the current amount possible to flow in the TFTs 8, even when the TFTs 8 are normal silicon transistor devices, and around seven digits smaller in value than the current amount thereof when the TFTs 8 are amorphous silicon (hydride) TFTs as in the embodiment. The rapidly-decreased amount possible to flow in the TFTs 8 is greatly smaller than the current amount i leak of the leak current including the dark current flowing in the radiation detection elements 7.

Therefore, when the voltage having the voltage value of the threshold value Vth with which the current amount possible to flow in the TFTs 8 is rapidly decreased is applied to the gate electrodes 8g of the TFTs 8, virtually, dark current is not discharged from the radiation detection elements 7 via the TFTs 8, but is accumulated in the radiation detection elements 7. This makes excess charge, such as the dark charge generated in the radiation detection elements 7, accumulated in the radiation detection elements 7 by the time irradiation starts.

Even when the voltage value of the ON-state voltage Von2 applied to the gate electrodes 8g of the TFTs 8 is increased to be more than the threshold value Vth, and the maximum current amount i max (Von2) of the ON-state current flowing in the TFTs 8 is increased, if the maximum current amount i max (Von2) of the ON-state current flowing in the TFTs 8 is smaller than the current amount i leak of the leak current including the dark current flowing in the radiation detection elements 7, the charge unable to be discharged from the radiation detection elements 7 is still accumulated therein.

Hence, in the embodiment, in order to make the maximum current amount i max (Von2) of the ON-state current flowing in the TFTs 8 a little more than the current amount i leak of the leak current including the dark current flowing in the radiation detection elements 7, the voltage value of the ON-state voltage Von2 is set at a low voltage value having some margin.

Thus, when the voltage value of the ON-state voltage Von2 is set at a low voltage value, as described below, even if electron-hole pairs are generated in the radiation detection elements 7 in response to the start of irradiation, the current value of the current which flows in the bias lines 9 and the like as a result of the electron-hole pairs being discharged from the radiation detection elements 7 can be limited to an amount which is a little more than the current amount i leak of the leak current flowing in the radiation detection elements 7.

Because the current amount flowing in the bias lines 9 or the like in response to the start of irradiation is limited, it becomes possible to limit the voltage fluctuation at the bias lines 9 and the signal lines 6, which is caused by the current flowing in the bias line 9 and signal lines 6 in response to the start of irradiation, to being smaller, and accordingly, it is possible to make the charge accumulated in the radiation detection elements 7 accompanying the voltage fluctuation further reduced.

As described above, when the voltage value of the ON-state voltage Von2, the voltage value being low, is set at a voltage value with which the maximum current amount i max (Von2) of the ON-state current flowing in the TFTs 8 becomes a little more than the current amount i leak of the leak current flowing in the radiation detection elements 7, even if the electron-hole pairs are discharged from irradiated radiation detection elements 7, and the voltage fluctuation occurs at the signal line 6 and the bias line 9, electric charge is hardly accumulated in the non-radiation detection elements 7 (in the regions R2 in FIG. 23B, for example) connected to the same signal line 6 and bias line 9 as the irradiated radiation detection elements 7, and virtually, image data having a significant value is not read therefrom, unlike in the conventional reset processing of the radiation detection elements 7.

Thus, in the embodiment, after the ON-state voltage Von1 having a high voltage value is applied to the gate electrodes 8g of the TFTs 8 in the reset processing of the radiation detection elements 7 performed before the radiation image capturing, the ON-state voltage Von is decreased from the ON-state voltage Von1 to the ON-state voltage Von2 having a lower voltage value than the voltage value of the ON-state voltage Von1 all at once so that the start of irradiation is detected. Accordingly, the phenomenon described above can be appropriately prevented from occurring.

Figure 24A:
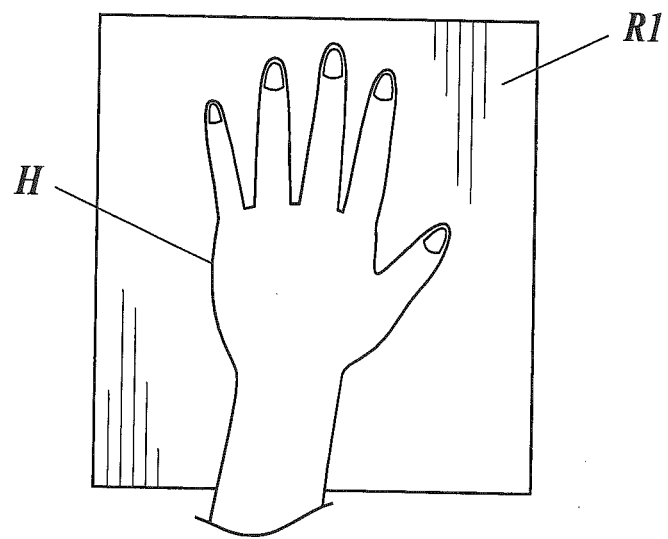
FIG. 24A shows a state in which a region including a subject is irradiated to photograph the subject.
Figure 24B:
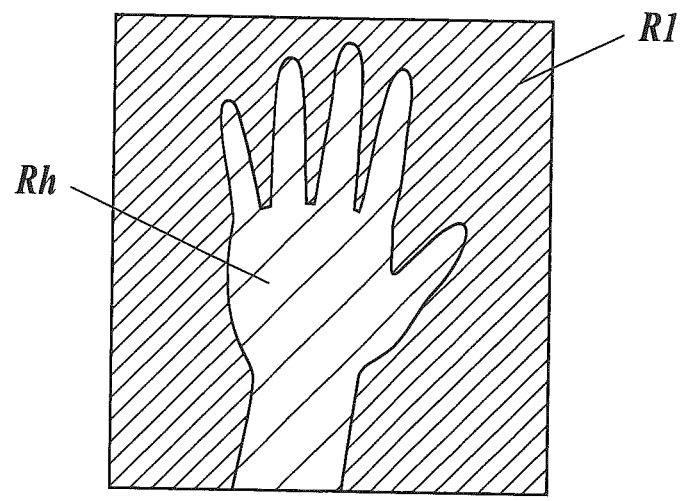
FIG. 24B is a diagram for explaining that image data having a significant value is generated in the subject-photographed region influenced by a directly-irradiated region around the subject-photographed region.

As described above, the phenomenon may occur not only in the non-irradiated radiation detection elements 7 adjacent to the irradiated radiation detection elements 7, but also, as shown in FIG. 24B, in weakly-irradiated radiation detection elements 7 in the region Rh. The region Rh is irradiated, but the radiation is weak because the radiation passes through a subject or the like. In addition, the region Rh is adjacent to the region 1 directly being irradiated.

The control configuration described in the embodiment can prevent image data having a significant value from being read from the weakly-irradiated radiation detection elements 7, which is caused in such a way that the voltage fluctuation occurs in the signal line 6 and/or the bias line 9 connected to the directly-irradiated radiation detection elements 7 in the region R1, and electric charge is accumulated in the weakly-irradiated radiation detection elements 7 in the region Rh, the weakly-irradiated radiation detection elements 7 connected to the same signal line 6 and bias line 9 as the directly-irradiated radiation detection elements 7.

Although not being shown in FIGS. 24A and 24B, the signal lines 6 and the bias lines 9 are arranged to extend in the right-left direction in FIGS. 24A and 24B. Furthermore, the ON-state voltage Von2 is set at a low voltage value as described above, but the maximum current amount i max (Von2) of the ON-state current flowing in the TFTs 8 is set at an amount a little more than the current amount i leak of the leak current including the dark current flowing in the radiation detection elements 7. Consequently, even if dark charge is generated in the radiation detection elements 7, the dark charge is discharged from the radiation detection elements 7 to the signal lines 6 and the bias lines 9. Accordingly, the dark charge is not accumulated in the radiation detection elements 7.

As described above, in order to perform the reset processing of the radiation detection elements 7, after applying the ON-state voltage Von1 having a high voltage value to the gate electrodes 8g of the TFTs 8 via the lines L1 to Lx of the scan lines 5 from the scan driving section 15, the control section 22 decreases the ON-state voltage Von to the ON-state voltage Von2 having a lower voltage value than the voltage value of the ON-state voltage Von1 all at once at the time T2 (shown in FIG. 11), turns off the switch 43d of the current detection section 43, and supplies power from the power supply section 44 to the differential amplifier 43c so as to start the current detection section 43.

Figure 12:
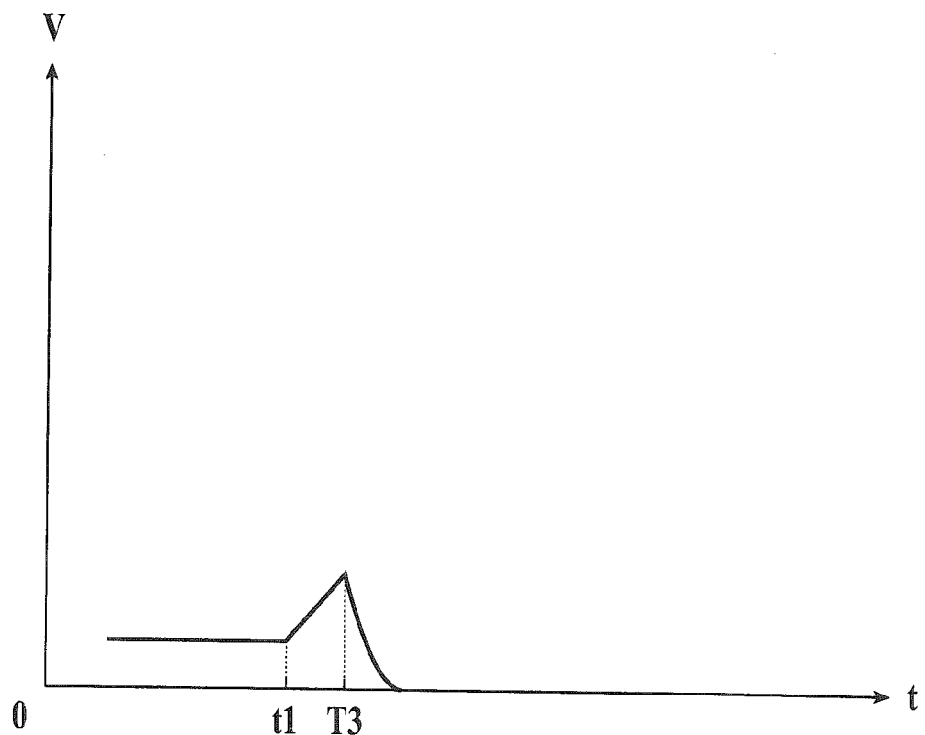
FIG. 12 is a graph showing an example of a voltage value corresponding to a current detected by the current detection section.

When irradiation starts in a state in which the voltage applied to the gate electrodes 8g of the TFTs 8 is kept at the ON-state voltage Von2 having a low voltage value (the irradiation start time is represented by "t1"), as described above, the charge generated in the radiation detection elements 7 by irradiation is discharged to the bias lines 9 and the signal lines 6. Accordingly, as shown in FIG. 12, the voltage value V corresponding to the current outputted from the differential amplifier 43c of the current detection section 43 starts to increase at the time t1.

As described above, when the voltage value of the ON-state voltage Von2 is set at a low voltage value, the current value which flows in the bias lines 9 and the like as a result of the electron-hole pairs being discharged from the radiation detection elements 7 is limited to a current amount which is a little more than the current amount i leak of the leak current flowing in the radiation detection elements 7. Hence, the current value (the voltage value V corresponding thereto, in the embodiment) of the current flowing in the bias lines 9 and the like increases only up to the current value (voltage value V) which corresponds to the above-described limited current value. Accordingly, as described above, the voltage fluctuation at the signal lines 6 and the bias lines 9 can be controlled to be a very small value.

Thus, in response to the start of irradiation, the current value outputted from the current detection section 43 increases, so that the control section 22 monitors the start of the irradiation. When the voltage value V outputted form the current detection section 43 increases, and, for example, the voltage value V exceeds a preset threshold value; the increase rate of the voltage value V exceeds a preset threshold value; or the voltage value V increases to the voltage value corresponding to the ON-state voltage Von2 having a low voltage value, the control section 22 detects that the irradiation starts.

If the TFTs 8 are kept on as described above, the charge generated in the radiation detection elements 7 is discharged to the signal lines 6 and the bias lines 9, and consequently, charge to be accumulated (image data) in the radiation detection elements 7 is reduced or not accumulated. Therefore, as shown in FIG. 11, when detecting that the irradiation starts by detecting the increase of the voltage value V (time T3), the control section 22 switches the voltage applied to the gate electrodes 8g of the TFTs 8 via the lines L1 to Lx of the scan lines 5 from the scan driving section 15, from the ON-state voltage Von2 having a low voltage value to the OFF-state voltage Voff all at once so as to turn off the TFTs 8, thereby making the radiation detection elements 7 in the charge accumulation mode.

When the voltage applied to the gate electrodes 8g of the TFTs 8 is switched to the OFF-state voltage Voff all at once (time T3), as shown in FIG. 12, the voltage value V corresponding to the current outputted from the current detection section 43 rapidly decreases.

In FIG. 12, the interval between the time t1, at which the irradiation starts, and the time T3, at which the voltage applied to the gate electrodes 8g of the TFTs 8 is switched to the OFF-state voltage Voff all at once, is enlarged in order to make the graph thereof easy to see. However, as a matter of fact, the interval therebetween is very short, and the time t1 and the time T3 are almost the same.

FIG. 12 shows a case where the voltage value V is decreased down to 0[V]. However, even after the TFTs 8 are turned off, it may happen that although the current is very weak, the current flowing in the bias lines 9 and the connection line 10 is detected, because of the charge generated in the radiation detection elements 7 by irradiation.

The reason why the current flows in the bias lines 9 even when the TFTs 8 are off is considered as follows. For example, when the TFT 8 in FIG. 8 is turned off, it can be considered that a closed loop is formed, the loop being from the scan line 5 to the bias power supply 14 via the TFT 8 and the radiation detection element 7, and in the loop, each of the TFT 8 and the radiation detection element 7 has a predetermined parasitic capacitance and is arranged in a shape of a capacitor. When electron-hole pairs are generated and accumulated in the i layer 76 (shown in FIG. 5) of the radiation detection element 7 by irradiation, the potential of the first electrode 74 (the potential being equal to the potential on the source electrode 8s side of the TFT 8) decreases as compared with the potential of the second electrode 78, to which a predetermined bias voltage is applied, in the radiation detection element 7. Therefore, the charge amounts accumulated in the first electrode 71 and the second electrode 78 of the radiation detection element 7 and the gate electrode 8g and the source electrode 8s of the TFT 8 change. In order to make up for the change, a current flows in the bias line 9, the line between the radiation detection element 7 and the TFT 8, and the scan line 5.

Thus, in the case where the current (or the voltage value V corresponding thereto) flowing in the bias lines 9 and the connection line 10 can still be detected even after the TFTs 8 are turned off, when the irradiation ends, the voltage value V corresponding to the current outputted from the current detection section 43 further decreases from the voltage value V by then. Hence, it is possible that the control section 22 detects the further decrease of the voltage value V which is already decreased at the time when all the TFTs 8 are turned off so as to detect the end of the irradiation.

However, it may happen that because of the weak current flowing in the bias lines 9 and the connection line 10, a voltage is generated between the terminals of the resistor 43a of the current detection section 43 and the predetermined bias voltage Vbias supplied to the radiation detection elements 7 fluctuates, or noise generated in the current detection section 43 is superposed on the bias voltage Vbias. In such a case, the charge amount (image data) generated and accumulated in the radiation detection elements 7 by irradiation may be influenced thereby.

In order to eliminate the bad influence resulted from the current detection section 43 being in operation after the irradiation starts, it is possible, after the start of the irradiation is detected at the time T3, to stop the operation of the current detection section 43 and short-circuit the switch 43d. Accordingly, the bad influence from the current detection section 43 is not exerted on the bias voltage Vbias applied to the radiation detection elements 7.

However, in this case, the end of the irradiation cannot be detected based on the voltage value V corresponding to the current outputted from the current detection section 43. Then, it is possible to judge that the irradiation ends when a preset time elapses from the time T3 at which the start of the irradiation is detected, and perform post processing.

To detect the end of the irradiation based on the current value outputted from the current detection section 43 (or the voltage value V corresponding thereto), the control section 22 stops the operation of the current detection section 43 at the time at which the end of the irradiation is detected, and short-circuits the switch 43d.

When the control section 22 detects that the irradiation ends (or judges that the irradiation ends because a predetermined time elapses from the start of the irradiation (time T2), the control section 22 performs the reading processing of image data from the radiation detection elements 7. In the reading processing, the control section 22 reads charge (image data) from the radiation detection elements 7 while switching the lines L1 to Lx of the scan lines 5 to which the ON-state voltage Von1 having a high voltage value is applied from the scan driving section 15, the voltage Von1 being for signal reading. Then, the control section 22 performs, for example, the charge-voltage conversion with the reading circuits 17 as described above, and stores the image data in the storage section 40.

It is possible to perform other various types of processing such as reset processing after the reading processing, and dark reading processing, too. However, those are known technologies, and hence the description thereof is omitted.

As described above, according to the radiation image capturing device 1 of the embodiment, in the reset processing of the radiation detection elements 7 performed before the radiation image capturing, the radiation image capturing device 1 applies the ON-state voltage Von1 having a high voltage value to the gate electrodes 8g of the TFTs 8 all at once, decreases the voltage value of the ON-state voltage Von all at once thereafter so as to apply the ON-state voltage Von2 having a low voltage value, monitor the current value (voltage value V) of the current outputted from the current detection section 43 while keeping the ON-state voltage Von2, and wait for the start of irradiation.

Thus, by applying the ON-state voltage Von1 having a high voltage value to the gate electrodes 8g of the TFTs 8 first, a state in which charge can be easily discharged from the radiation detection elements 7 is made. Consequently, the excess charge such as dark charge accumulated in the radiation detection elements 7 is certainly discharged. Accordingly, the reset efficiency of the radiation detection elements 7 can be increased.

Furthermore, by switching the ON-state voltage Von, which is to be applied, to the ON-state voltage Von2 having a low voltage value thereafter, the charge discharged from the radiation detection elements 7, namely, the current value, can be controlled not to be too large by the time when the generation of the charge starts in the radiation detection elements 7 in response to the start of the irradiation. Because the current flows out from the radiation detection elements 7 is controlled, it becomes possible to prevent the fluctuation of the reference potential $V_0$ applied to the first electrodes 74 of the radiation detection elements 7 and the bias voltage Vbias applied to the second electrodes 78 thereof from occurring, the fluctuation thereof which may occur accompanying the current flowing out.

Accordingly, it can be appropriately avoided that the non-irradiated radiation detection elements 7 connected to the signal line 6 and the bias line 9 to which the strongly-irradiated radiation detection elements 7 are connected (namely, the radiation detection elements 7 in the regions R2 in FIG. 23B, for example) are influenced by the region 1 near the non-irradiated radiation detection elements 7 and strongly irradiated, and the weakly-irradiated radiation detection elements 7 connected to the signal line 6 and the like to which the directly-irradiated radiation detection elements 7 are connected, and weakly irradiated as the radiation passes through a subject H (namely, the radiation detection elements 7 in the region Rh in FIG. 24B, for example) are influenced by the region R1 near the weakly-irradiated radiation detection elements 7 and directly irradiated.

Therefore, a captured image of the bone structure or the internal tissue of a hand of a patient in the region Rh in which the subject H of the hand of the patient is photographed as shown in FIG. 24A is not influenced by the region R1 near the region Rh and directly irradiated. Consequently, the region Rh is prevented from being blackish. Therefore, for example, a lesioned part which is originally hard to be seen in a radiation image can be captured with excellent contrast. Hence, a doctor or the like can appropriately judge whether there is a lesioned part or not.

Even when, as described in the embodiment, the ON-state voltage Von2, the voltage value of which is decreased, is set at a voltage value with which the maximum current amount i max (Von2) of the ON-state current flowing in the TFTs 8 becomes a little more than the current amount i leak of the leak current including the dark current flowing in the radiation detection elements 7, and the ON-state voltage Von2 is applied to the gate electrodes 8g of the TFTs 8, there may be a TFT 8 in which the maximum current amount i max (Von2) of the ON-state current dose not become a little more than the current amount i leak of the leak current because of the manufacturing error or the like.

In such a TFT 8, even when the ON-state voltage Von2 having a low voltage value is applied to the gate electrode 8g thereof, the ON-state current does not flow enough, and hence dark charge may be accumulated in the radiation detection element 7 to which the TFT 8 is connected.

Figure 13:
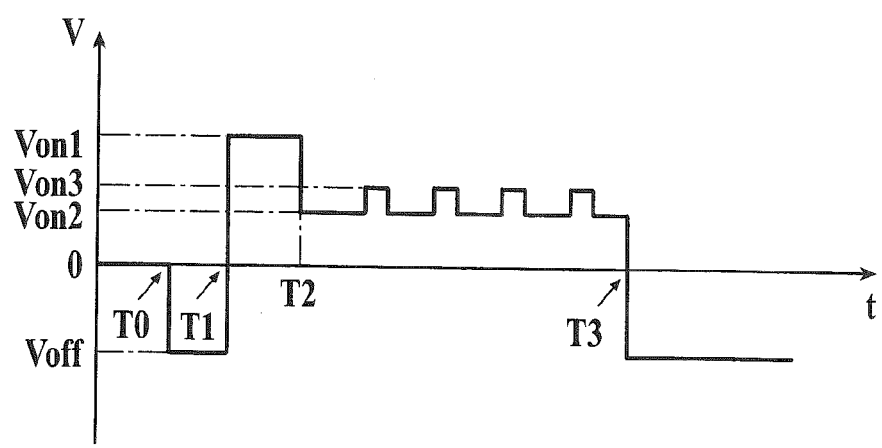
FIG. 13 is a timing chart in reset processing performed before radiation image capturing according to a modification.

Then, in order to prevent dark charge from being accumulated in the radiation detection elements 7, for example, as shown in FIG. 13, it is possible, after decreasing the voltage value of the ON-state voltage Von applied from the scan driving section to the gate electrodes 8g of the TFTs 8 via the lines L1 to Lx of the scan lines 5 all at once so as to apply the ON-state voltage Von2 having a low voltage value, to perform an operation to increase the voltage value of the ON-state voltage Von with a predetermined voltage width to be an ON-state voltage Von3, and decrease the ON-state voltage Von3 so as to return to the ON-state voltage Von2 one time or a plurality of times, before the start of irradiation is detected.

By having such a configuration, even in the TFT 8 in which when the ON-state voltage Von2 is applied to the gate electrode 8g, the maximum current amount i max (Von2) of the ON-state current does not become a little more than the current amount leak of the leak current, the maximum current amount i max (Von2) of the ON-state current becomes a little more than the current amount i leak of the leak current by the ON-state voltage Von3, which is higher than the ON-state voltage Von2 for the predetermined voltage width, being applied thereto. Accordingly, it becomes possible to discharge dark charge accumulated in a radiation detection element 7 to which the TFT 8 is connected.

Therefore, even in the radiation detection element 7 to which such a TFT 8 is connected, like in the other radiation detection elements 7, it becomes possible to sufficiently reduce the amount of dark charge remaining in the radiation detection element 7 before the irradiation starts. Accordingly, a radiation image obtained by the radiation image capturing can be prevented from being badly influenced from the accumulation of dark charge in the radiation detection elements 7.

Second Embodiment

As described above, the cause of the generation of image data having a significant value in the regions R2 which are adjacent to the strongly-irradiated region R1 shown in FIG. 23A in the signal extending direction of the signal lines 6 not shown in FIGS. 23A and 23B (the up-down direction in FIG. 23B) is considered that because the electrons and the holes generated in the radiation detection elements 7 of the region R1 are discharged to the signal lines 6 and the bias lines 9, the reference potential $V_0$ applied to the first electrodes 74 of the radiation detection elements 7 and the bias voltage Vbias applied to the second electrodes 78 thereof fluctuate.

Therefore, in the first embodiment, in the reset processing of the radiation detection elements 7 performed before the radiation image capturing, after the ON-state voltage Von1 having a predetermined voltage value is applied to the gate electrodes 8g of the TFTs 8 via the lines L1 to Lx of the scan lines 5 from the scan driving section 15 (shown in FIG. 7) so as to certainly discharge the excess charge such as dark charge accumulated in the radiation detection elements 7, the ON-state voltage Von is decreased to the ON-state voltage Von2 having a lower voltage value than the voltage value of the ON-state voltage Von1 all at once, and kept.

By having such a configuration, the charge which is generated in the radiation detection elements 7 by irradiation, and discharged therefrom, namely, the current value, is controlled not to be too large, and the fluctuation of the reference potential $V_0$ applied to the first electrodes 74 of the radiation detection elements 7 and the bias voltage Vbias applied to the second electrodes 78 thereof are controlled not to occur, and accordingly, image data having a significant value is prevented from being generated in the regions R2 adjacent to the strongly-irradiated regions R1, as described above.

In the second embodiment of the present invention, it is described that, of the reference potential $V_0$ and the bias voltage Vbias, by particularly making the fluctuation occurring in the reference potential $V_0$ smaller, image data having a significant value can be more appropriately prevented from being generated in the regions R2 adjacent to the strongly-irradiated region R1.

Figure 14:
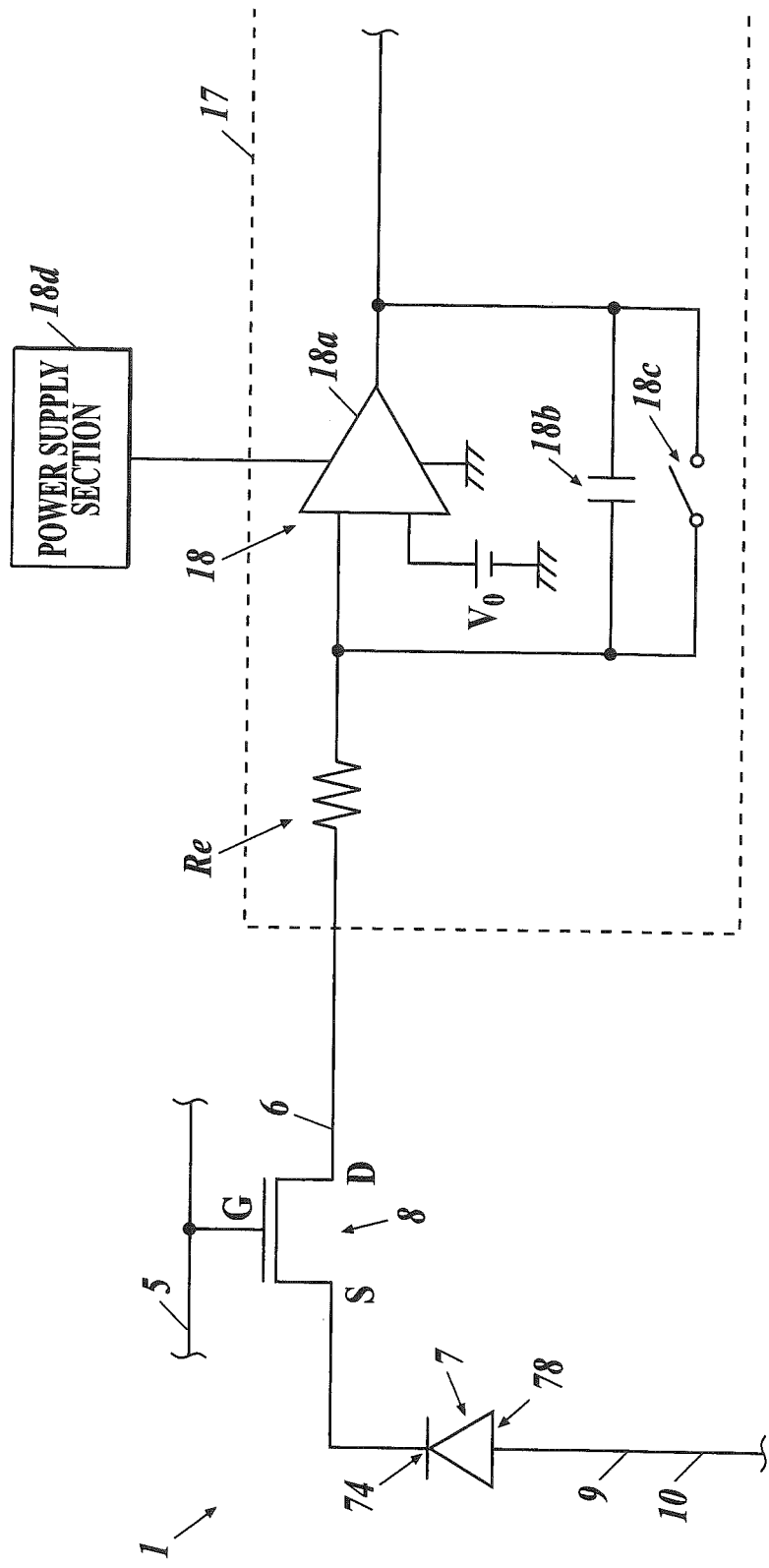
FIG. 14 is a block diagram showing an equivalent circuit of an amplifier circuit provided with a resistor on an input terminal side of an operational amplifier.
Figure 15:
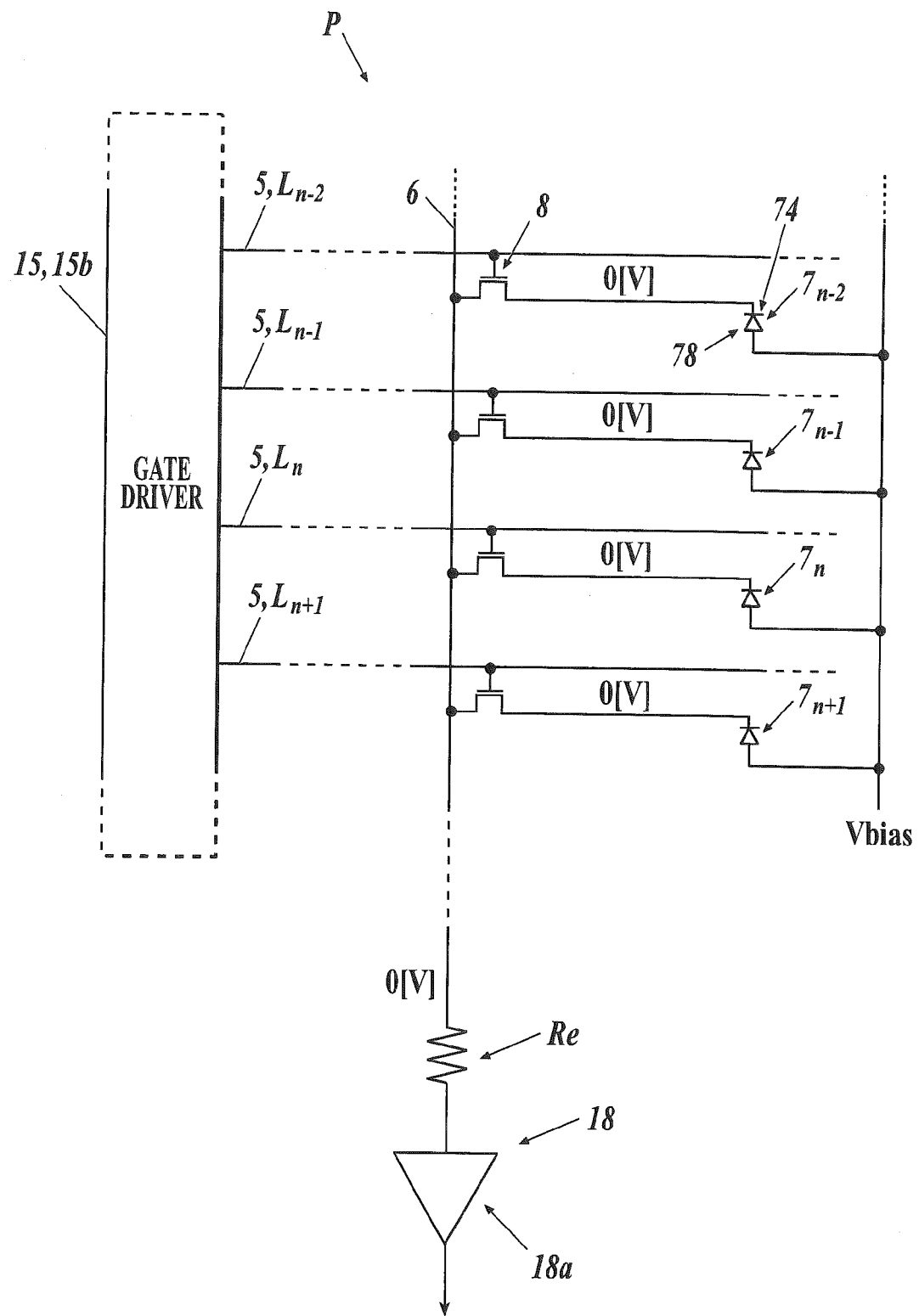
FIG. 15 is a diagram for explaining that a reference potential is applied to a first electrode side of the radiation detection element, a source electrode and a drain electrode of the TFT, a signal line, and the like, before the irradiation starts.

Although not being shown in FIGS. 7 and 8, in order to reduce power consumption or the like, as shown in FIGS. 14 and 15, each reading circuit 17 is often configured in such a way that the input terminal of the operational amplifier 18a of the amplifier circuit 18, namely, the reverse input terminal, is connected to the signal line 6 via a resistor Re. In order to reduce power consumption, the resistance value of the resistor Re is usually set at a high value.

As shown in FIG. 14, the reference potential $V_0$ is applied to the non-reverse input terminal of the operational amplifier 18a. Hence, when the current does not flow in the signal line 6, the reference potential $V_0$ is applied to the signal line 6 via the operational amplifier 18a too. The correlated double sampling circuit 19 and the like are not shown in FIGS. 14 and 15 and also in FIGS. 16 to 18 described below.

In the following, a phenomenon which occurs because the amplifier circuit 18 has the resistor Re is described.

As shown in FIGS. 11 and 13, in the reset processing of the radiation detection elements 7 performed before the radiation image capturing, when the voltage applied to the lines L1 to Lx of the scan lines 5 from the scan driving section 15 is decreased from the ON-state voltage Von1 to the ON-state voltage Von2 all at once, and accordingly the ON-state voltage Von2 is being applied to the gate electrodes of the TFTs 8, as described above, the TFTs 8 are on, and the current can flow from the radiation detection elements 7 via the TFTs 8 to the signal lines 6 with the current amount which is a little more than the current amount i leak of the leak current.

Then, as shown in FIG. 15, the reference potential $V_0$ is applied to the first electrode 74 side of the radiation detection elements 7, the source electrodes 8s and the drain electrodes 8d of the TFTs 8, the signal lines 6, and the like, and the bias voltage Vbias is applied to the second electrode 78 side of the radiation detection elements 7, the bias lines 9, and the like.

Figure 16:
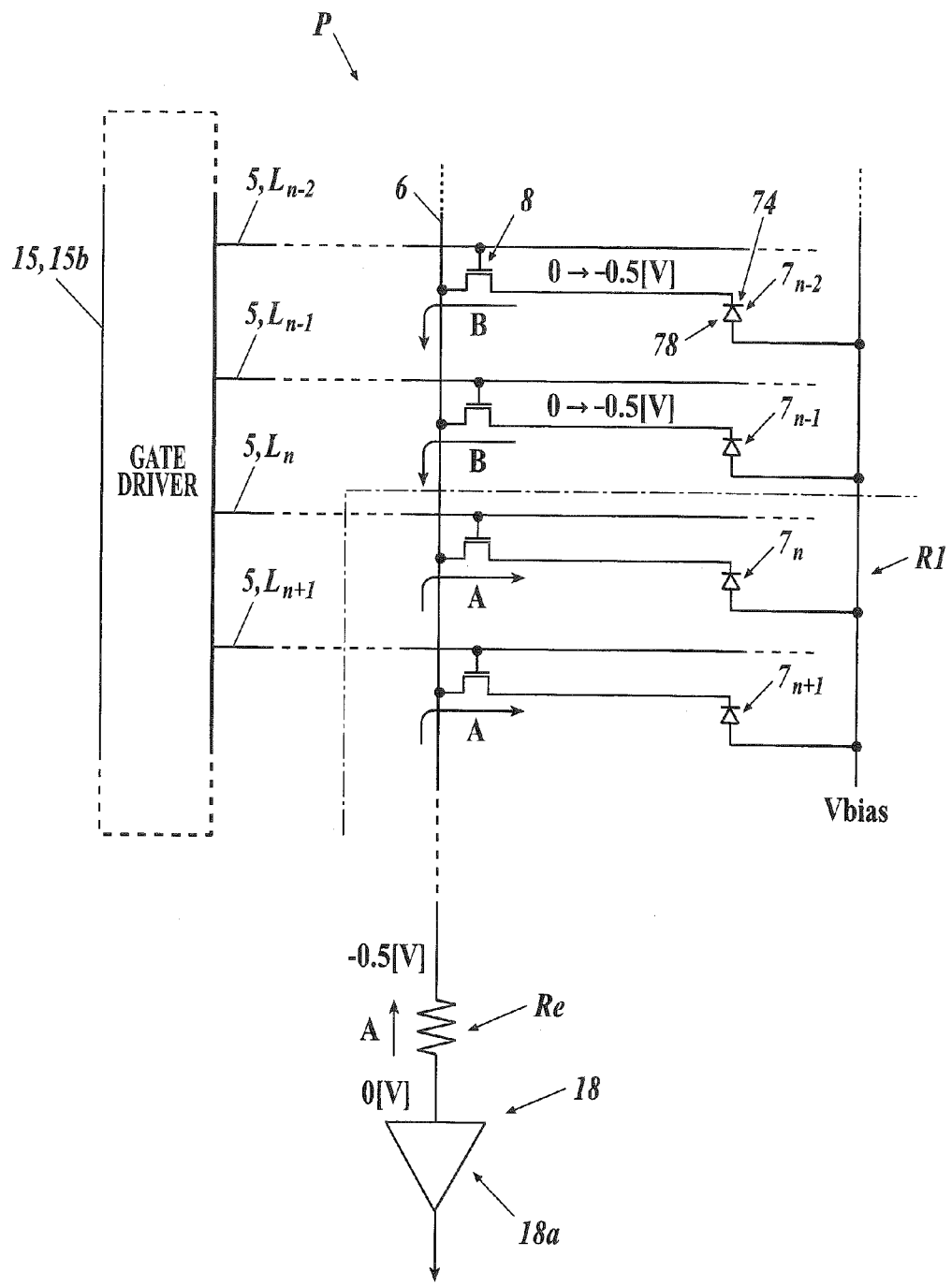
FIG. 16 is a diagram for explaining that a current flows into each irradiated radiation detection element, and a potential difference is generated between both terminals of the resistor, and consequently, a potential on the first electrode side of each non-irradiated radiation detection element decreases.
Figure 17:
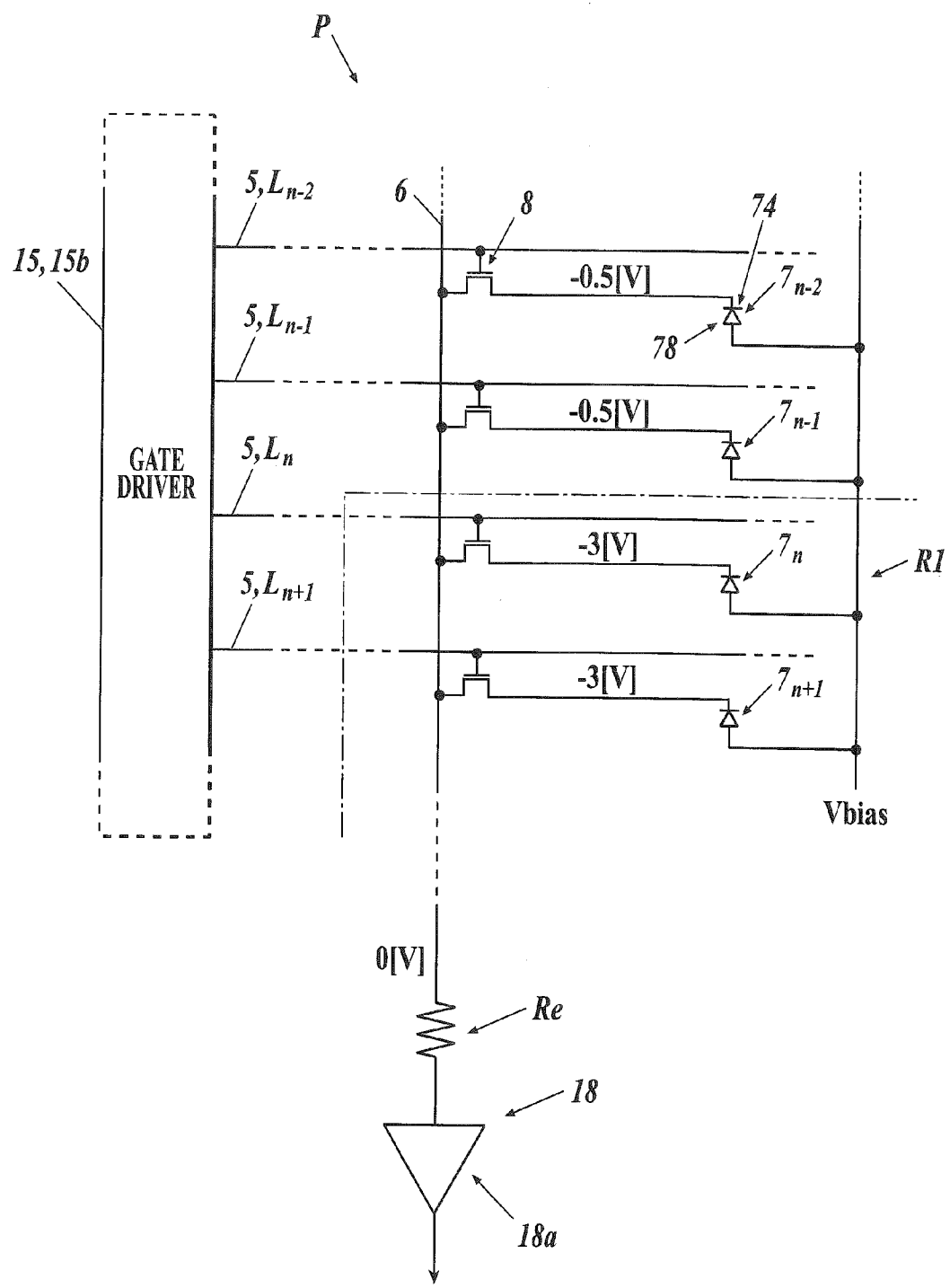
FIG. 17 is a diagram for explaining that when each TFT is turned off in the state shown in FIG. 16, the potential on the first electrode side of each non-irradiated radiation detection element is fixed at a lower potential than the reference potential.

FIG. 15 and FIGS. 16 and 17 described below show that the reference potential $V_0$ is set at 0[V]. However, as described above, the reference potential $V_0$ can be set at another value, and hence can be set at an appropriate value. Furthermore, FIG. 15 shows only the radiation detection elements 7 connected to one signal line 6 via the TFTs 8. However, the same applies to the radiation detection elements 7 connected to the other signal lines 6.

In the state shown in FIG. 15, when, for example, irradiation starts to the radiation detection elements $7n, 7n+1, \ldots$ in the region R1 of the detection section P as shown in FIG. 16, electron-hole pairs are generated in the radiation detection elements $7n, 7n+1, \ldots$, and the potential on the first electrode 74 side decreases as compared with the potential on the second electrode 78 side.

Furthermore, at the time of the start of the irradiation, the ON-state voltage Von2 is applied to the gate electrodes 8g of the TFTs 8 so that the TFTs 8 are on. Hence, as described above, when the potential difference between the first electrode and the second electrode of each of the radiation detection elements $7n, 7n+1, \ldots$ changes, the electrons are discharged to the signal line 6 in the embodiment. In terms of the current, the current (i.e. photocurrent) flows in the signal line 6 so as to flow into the radiation detection elements $7n, 7n+1, \ldots$ (expressed by arrows A in FIG. 16).

At the time, as described above, the current amount of the current flowing into the radiation detection elements $7n, 7n+1, \ldots$ from the signal line 6 is a little more than the current amount i leak of the leak current, and hence the current amount is very small. However, because the current flows into numerous radiation detection elements $7n, 7n+1, \ldots$, which are irradiated, the current flowing in the signal line 6 is a current having a certain amount.

In such a situation, when the resistance value of the resistor Re of the amplifier circuit 18 is a high value as described above, a potential difference is generated between the terminals of the resistor Re. That is, the potential at the terminal of the resistor Re, the terminal connected to the operational amplifier 18a, keeps the reference potential $V_0$ (0[V]), but the potential at the other terminal of the resistor Re (the terminal connected to the signal line 6) decreases, for example, to −0.5[V], and hence −0.5[V] is applied to the signal line 6.

Because the potential at the first electrode 74 side of each of the non-irradiated radiation detection elements $7n-1, 7n-2, \ldots$ is originally 0[V], the current flows from the radiation detection elements $7n-1, 7n-2, \ldots$ to the signal line 6 (expressed by arrows B in FIG. 16). Then, the potential at the first electrode 74 side of each of the radiation detection elements $7n-1, 7n-2, \ldots$ decreases to −0.5[V] which is the same as the potential at the signal line 6.

After the above-described phenomenon occurs within a very short period of time right after the irradiation starts, the OFF-state voltage Voff is applied to the lines L1 to Lx of the scan lines 5 from the scan driving section 15 all at once. Consequently, TFTs 8 are turned off all at once, and charge is accumulated in the radiation detection elements 7 (charge accumulation mode).

At the time, as shown in FIG. 17, in the radiation detection elements $7n, 7n+1, \ldots$ in the irradiated region R1, as described above, when irradiation starts, the potential at the first electrode 74 side decreases as compared with the potential at the second electrode 78 side (i.e. the bias voltage Vbias). Hence, when irradiation starts, and the TFTs 8 are turned off all at once to move to the charge accumulation mode, the potential at the first electrode 74 side is not the reference potential $V_0$ (0[V]), but becomes, for example, −3[V]. Then, more electron-hole pairs are generated in the radiation detection elements $7n, 7n+1, \ldots$ by irradiation, and the potential at the first electrode 74 side further decreases.

On the other hand, the radiation detection elements $7n-1, 7n-2, \ldots$ in regions other than in the region R1, although not being irradiated, as described above, when irradiation starts to the region R1, the potential at the first electrode 74 side changes from the reference potential $V_0$ of 0[V] to, for example, −0.5[V] within a very short period of time, and then TFTs 8 are turned off. Therefore, as shown in FIG. 17, at the time when all the TFTs 8 are turned off, the potential at the first electrode 74 side of each of the radiation detection elements 7n–1, 7n–2, . . . is fixed at not the reference potential $V_0$ of 0[V] but at –0.5[V].

Then, in the reading processing of image data from the radiation detection elements 7 performed after the irradiation, when the TFTs 8 are turned on while the reference potential $V_0$ of 0[V] is applied to the signal lines 6, the current flows from the signal line 6 side into the radiation detection elements 7n–1, 7n–2, . . . having a potential at the first electrode 74 side of not the reference potential $V_0$ (0[V]) but –0.5[V]. Then, the charge in accordance with the current is accumulated in the capacitors 18b of the amplifier circuits 18 of the reading circuits 17, and the voltage value in accordance with the accumulated charge is outputted from the amplifier circuits 18. Thus, although the radiation detection elements 7n–1, 7n–2, . . . are not irradiated, image data having a significant value is read therefrom.

In the above-described phenomenon occurring within a very short period of time which is from the time the irradiation starts to the time all the TFTs 8 are turned off, in particular, in the case of the strongly-irradiated region R1, the current value of the current flowing in the signal lines 6 becomes large, and the voltage drop caused by the resistors Re of the amplifier circuits 18 becomes large too. Consequently, the potential at the first electrode 74 side of each of the non-irradiated radiation detection elements 7n–1, 7n–2, . . . also fluctuates more largely, and accordingly, the image data read from the radiation detection elements 7n–1, 7n–2, . . . has a larger significant value.

When such a phenomenon occurs, like the case shown in FIG. 23B, an image based on the image data having a significant value also appears in the regions R2 which are not irradiated but adjacent to the region R1 in the signal line direction (in the vertical direction in FIG. 23B), the region R1 being irradiated.

Figure 18:
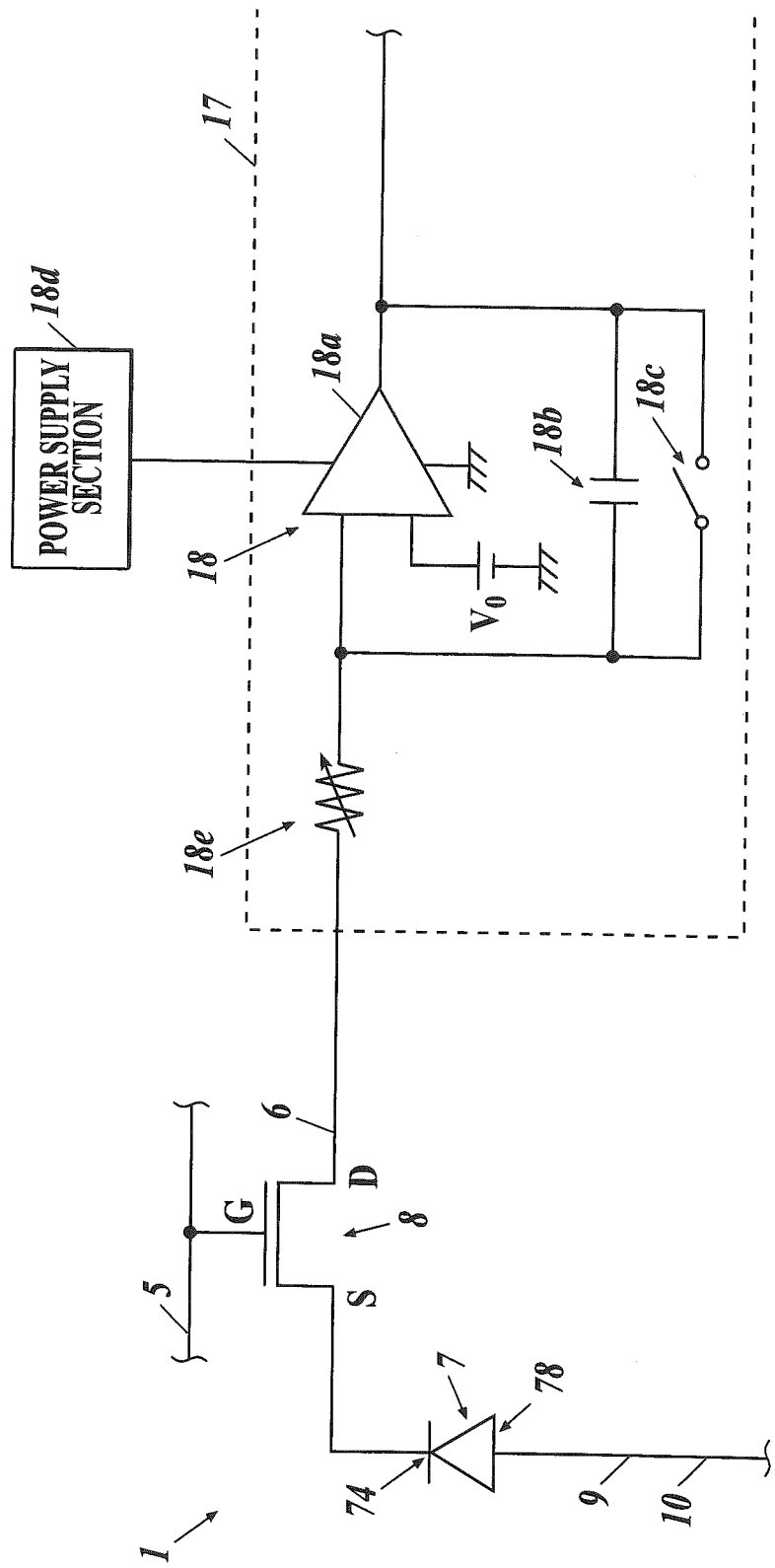
FIG. 18 is a block diagram showing an equivalent circuit of an amplifier circuit provided with a variable resistor on an input terminal side of an operational amplifier according to the second embodiment.

In order to prevent such a phenomenon from occurring, in the radiation image capturing device 1 of the embodiment, as shown in FIG. 18, the input terminal of each amplifier circuit 18 of each reading circuit 17, namely, the reverse input terminal thereof, is connected to the signal line 6 via the variable resistor 18e.

Furthermore, at least while the control section 22 monitors the current value (or the voltage value V corresponding thereto) of the current flowing, for example, in the connection line 10 for the bias lines 9, the current value which is outputted from the current detection section 43, in a state in which the ON-state voltage Von applied to the lines L1 to Lx of the scan lines 5 from the scan driving section 15 is decreased from the ON-state voltage Von1 to the ON-state voltage Von2 all at once after the reset processing of the radiation detection elements 7; and waits for the start of the irradiation, a resistance value of the variable resistor 18e varies to be in a low state.

By having such a configuration, even when a current amount being a little more than the current amount i leak of the leak current flows from the signal line 6 into the radiation detection elements 7n, 7n+1, . . . in the irradiated region R1 in response to the start of the irradiation, and the current flowing in the signal line 6 becomes a current having a certain amount, the potential difference generated between the terminals of each variable resistor 18e is very small, and the potential drop at the first electrode 74 side of each of the non-irradiated radiation detection elements 7n–1, 7n–2, . . . is very small too.

After that, even when the TFTs 8 are turned off, the potential at the first electrode 74 side of each of the radiation detection elements 7n–1, 7n–2, . . . is fixed at a potential a little smaller than the reference potential $V_0$ of 0[V]. Hence, in the reading processing of image data from the radiation detection elements 7 performed thereafter, only image data having a value of near 0 is read from the radiation detection elements 7n–1, 7n–2, . . . .

As described above, according to the radiation image capturing device 1 of the second embodiment, by using the variable resistor 18e as a resistor at the input terminal side of each amplifier circuit 18 of each reading circuit 17, and varying the resistance value of the variable resistor 18e to be low by the time of the start of the irradiation, it becomes possible to make the fluctuation occurring at the reference potential $V_0$ applied to the signal lines 6 smaller. Accordingly, image data having a significant value can be appropriately prevented from being generated in the regions R2 adjacent to the strongly-irradiated region R1.

It is also possible to make the resistance value of each variable resistor 18e smaller right before the radiation image capturing device 1 is irradiated. However, in the reset processing of the radiation detection elements 7, the reset efficiency increases more when excess charge discharged from the radiation detection elements 7 to the signal lines 6 can easily flow in the signal lines 6. Also, there is a risk that the noise generated by varying the resistance value of each variable resistor 18e when irradiation starts and the charge accumulation mode is set, and the noise generated in the variable resistor 18e itself, are accumulated in the radiation detection elements 7 as noise charge. In view of the circumstances, it is preferable to decrease the resistance value of the variable resistor 18e at the time when the reset processing of the radiation detection elements 7 starts or before that.

Furthermore, in the reading processing of the image data from the radiation detection elements 7, like in normal processing, the resistance value of the variable resistor 18e may be varied to be a high value. Alternatively, as described above, in order to prevent the noise generated by varying the resistance value of the variable resistor 18e and the noise generated in the variable resistor 18e itself from being read as noise charge, the resistance value of the variable resistor 18e may be kept low.

Third Embodiment

By the way, conventionally, in order to switch a radiation image capturing device to the charge accumulation mode, the voltage applied to the gate electrodes 8g of the TFTs 8 is switched from the ON-state voltage Von1 having a predetermined positive voltage value (shown in FIG. 11) to the OFF-state voltage Voff having a predetermined negative voltage value. However, when such a switching is carried out, a drive circuit for applying a voltage to the TFTs 8 in the gate driver 15b (shown in FIG. 7) may be overloaded, and accordingly, the drive circuit may be damaged or broken.

Furthermore, like in the first embodiment and the second embodiment, even when the ON-state voltage Von1 having a predetermined positive voltage value is applied to the gate electrodes 8g of the TFTs 8 all at once, and then the ON-state voltage Von1 is decreased all at once so that the ON-state voltage Von2 is applied thereto, there is still a possibility that the drive circuit in the gate driver 15b is overloaded, and the drive circuit is damaged or broken when the start of the irradiation is detected and the voltage is switched to the OFF-state voltage Voff all at once.

Hence, in the third embodiment, the radiation image capturing device is described, the radiation image capturing device which can obtain the same effects as that of the first and second embodiments, and also can prevent the gate driver thereof from being damaged or broken, which may occur when the start of the irradiation is detected and the voltage applied to the switch section is switched at the time.

The configurations of the radiation image capturing device 1 and the functional components thereof in the third embodiment are the same as those in the first and second embodiments. The functional components in the third embodiment are donated by the same numeral references as those in the first and second embodiments. The description of the functional components is omitted, but the configuration of the scan driving section 15 is described in more detail.

Figure 19:
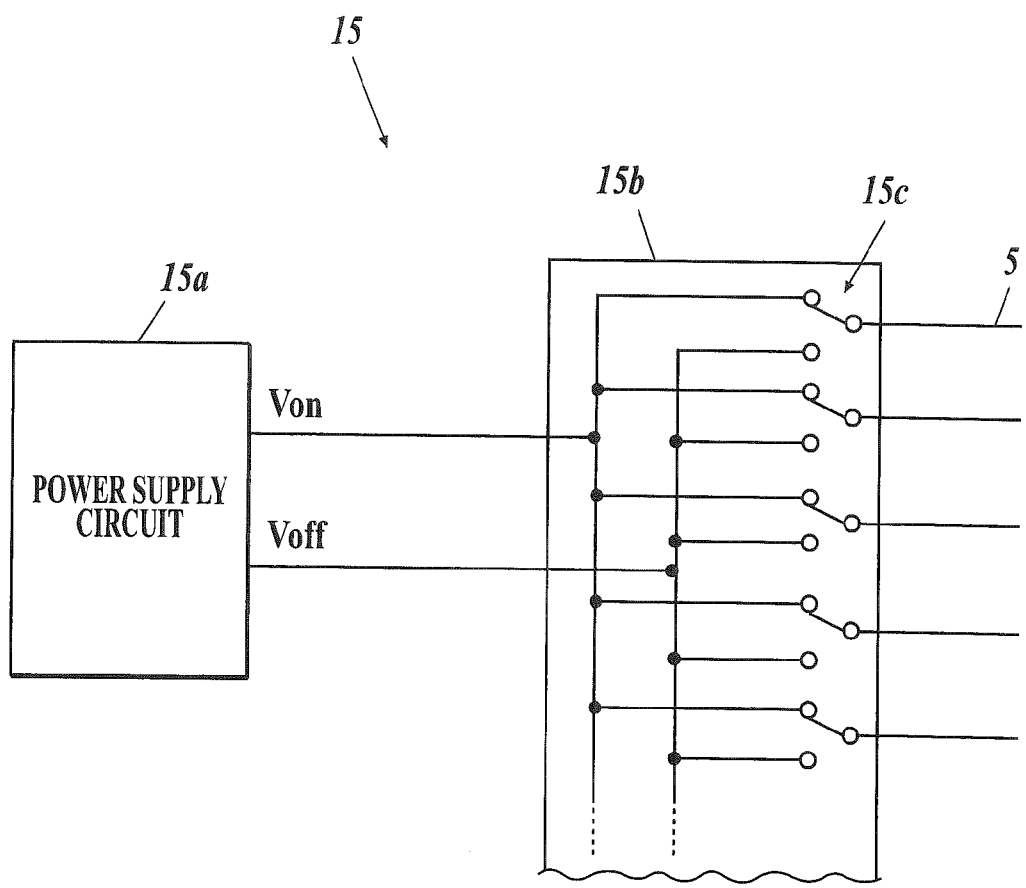
FIG. 19 schematically shows the configuration of a scan driving section.

As schematically shown in FIG. 19, the power supply circuit 15a of the scan driving section 15 supplies the ON-state voltage Von and the OFF-state voltage Voff, which are applied to the scan lines 5 from the gate driver 15b, to the gate driver 15b. The gate driver 15b of the scan driving section 15 selectively switches the ON-state voltage Von and the OFF-state voltage Voff, which are supplied from the power supply circuit 15a, by a switching operation of each of switch elements 15c, so as to apply the ON-state voltage Von or the OFF-state voltage Voff to each of the scan lines 5.

The power supply circuit 15a of the scan driving circuit 15 has a function to adjust the voltage values of the ON-state voltage Von and the OFF-state voltage Voff, so as to switch the voltage values of the ON-state voltage Von and the OFF-state voltage Voff applied to the gate electrodes 8g of the TFTs 8 via the lines L1 to Lx of the scan lines 5.

In the following, for example, the control of the ON-state voltage Von and the OFF-state voltage Voff applied to the gate electrodes 8g of the TFTs 8 in the reset processing of the radiation detection elements 7 and in the detection of the start of the irradiation in the radiation image capturing device 1 of the third embodiment is described. Also, the operation of the radiation image capturing device 1 of the third embodiment is described.

In the third embodiment too, the control section 22 performs the reset processing of the radiation detection elements 7 before the radiation image capturing by applying the ON-state voltage Von having a predetermined voltage value to the gate electrodes 8g of the TFTs 8 via the lines L1 to Lx of the scan lines 5 from the scan driving section 15 all at once. After that, the control section 22 decreases the ON-state voltage Von1 to the ON-state voltage Von2 all at once, monitors the current value (or the voltage value V corresponding thereto) of the current outputted from the current detection section 43 while keeping the ON-state voltage Von2, and waits for the start of the irradiation. In these points, the third embodiment is the same as the first and second embodiments.

In the third embodiment too, the voltage value of the ON-state voltage Von2, the voltage value being decreased, is set at a voltage value with which when the ON-state voltage Von2 is applied to the gate electrodes 8g of the TFTs 8 to turn on the TFTs 8, the maximum current amount i max (Von2) of the ON-state current flowing in the TFTs 8 becomes a little more than the current amount i leak of the leak current including the dark current flowing in the radiation detection elements 7.

On the other hand, when the control section 22 detects the start of the irradiation based on the current value detected by the current detection section 43, the scan driving section 15 needs to switch the voltage applied to the gate electrodes 8g of the TFTs 8 from the ON-state voltage Von2 to the OFF-state voltage Voff in order to stop discharge of the charge from the radiation detection elements 7 and to switch to the charge accumulation mode.

However, at the time, if the voltage applied to the gate electrodes 8g of the TFTs 8 are switched from the ON-state voltage Von2 to the OFF-state voltage Voff having a predetermined negative voltage value all at once, the not-shown drive circuit in the gate driver 15b of the scan driving section 15 may be overloaded, and the drive circuit may be damaged or broken, as described above. The drive circuit of the gate driver 15b may be overloaded when the ON-state voltage Von is switched to the OFF-state voltage Voff. The drive circuit of the gate driver 15b is not overloaded when the voltage value of the ON-state voltage Von itself or the voltage value of the OFF-state voltage Voff itself is changed.

Hence, in the third embodiment, the scan driving section 15 increases the voltage value of the OFF-state voltage Voff in advance (hereinbelow, the OFF-state voltage Voff having the increased voltage value is referred to as "Voff2"), the OFF-state voltage Voff to which the ON-state voltage Von2 is switched, and when the control section 22 detects the start of the irradiation, switches the voltage applied to the gate electrodes 8g of the TFTs 8 from the ON-state voltage Von2 to the OFF-state voltage Voff2 having the increased voltage value. After that, the scan driving section 15 decreases the OFF-state voltage Voff from the OFF-state voltage Voff2 having the increased voltage value to the OFF-state voltage Voff1 having the original predetermined negative voltage value, so as to make the TFTs 8 completely off.

In this case, the increased voltage value of the OFF-state voltage Voff2 is set in such a way that the difference between the voltage value of the ON-state voltage Von2 and the voltage value of the OFF-state voltage Voff2 is a difference with which the gate driver 15b is not damaged or broken when the ON-state voltage Von2 is switched to the OFF-state voltage Voff2.

However, as described above, the voltage value of the ON-state voltage Von2, the voltage value being decreased, is set at a voltage value with which the maximum current amount i max (Von2) of the ON-state current flowing in the TFTs 8 becomes a little more than the current amount i leak of the leak current including the dark current flowing in the radiation detection elements 7. Hence, it may be difficult to set the difference between the voltage value of the OFF-state voltage Voff2 and the voltage value of the ON-state voltage Von2 at a difference with which the gate driver 15b is not damaged or broken when the above-described switching is performed.

Then, it is possible to further decrease the decreased voltage value of the ON-state voltage Von2 to an ON-state voltage Von4 having a further lower voltage value, when the control section detects the start of the irradiation, and then to switch the ON-state voltage Von4 to the OFF-state voltage Voff2 having the increased voltage value. In this case too, after that, the OFF-state voltage Voff is switched from the OFF-state voltage Voff2, which has the increased voltage value, to the OFF-state voltage Voff1, which has the original predetermined negative voltage value, so as to make the TFTs 8 completely off.

Furthermore, in the case, the further-decreased voltage value of the ON-state voltage Von4 is set in such a way that the difference between the voltage value of the OFF-state voltage Voff2, the voltage value being increased, and the voltage value of the ON-state voltage Von4 is a difference with which the gate driver 15b is not damaged or broken when the ON-state voltage Von4 is switched to the OFF-state voltage Voff2.

In the following, the control of the ON-state voltage Von and the OFF-state voltage Voff applied to the gate electrodes 8g of the TFTs 8 in the reset processing of the radiation detection elements 7 and in the detection of the start of the irradiation in the third embodiment is described in reference with the timing charts of FIG. 20 and the like.

In the third embodiment, as schematically shown in FIG. 19, the ON-state voltage Von and the OFF-state voltage Voff are individually supplied from the power supply circuit 15a of the scan driving section 15 to the gate driver 15b thereof. The gate driver 15b selectively switches the ON-state voltage Von and the OFF-state voltage Voff by the switching operation of each of the switch elements 15c, so as to apply the ON-state voltage Von or the OFF-state voltage Voff to each of the lines L1 to Lx of the scan lines 5. The power supply circuit 15a can adjust the voltage values of the ON-state voltage Von and the OFF-state voltage Voff supplied to the gate driver 15.

Figure 20:
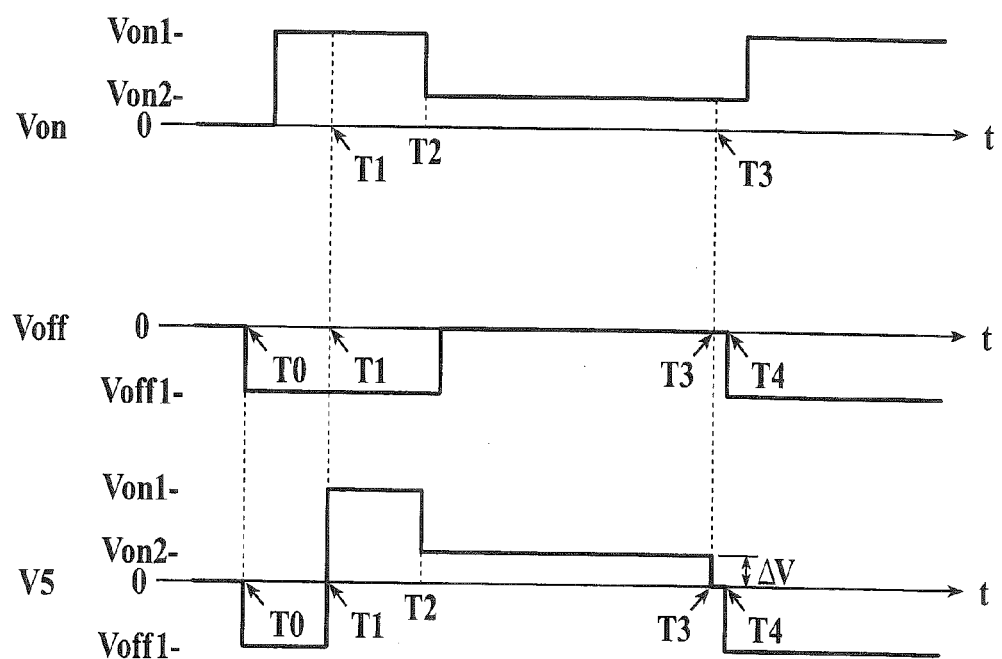
FIG. 20 shows examples of a timing chart of an ON-state voltage (upper part) and an OFF-state voltage (middle part) in the reset processing or the like of each radiation detection element, and a voltage value applied to each scan line by switching the ON-state voltage and the OFF-state voltage (lower part)

As shown in FIG. 20, when an operator presses the power supply switch 36 (shown in FIG. 1) or the like to start the radiation image capturing device 1 at the time T0, the ON-state voltage Von and the OFF-state voltage Voff supplied from the power supply circuit 15a are set at predetermined voltage values. In the third embodiment, the ON-state voltage Von supplied at this point of time is set at the above-described ON-state voltage Von1 having the highest predetermined positive voltage value, and the OFF-state voltage Voff is set at the above-described OFF-state voltage Voff1 having the lowest predetermined negative voltage value. The OFF-state voltage Voff1 has the same voltage value as the OFF-state voltage Voff in the first and second embodiments.

When the radiation image capturing device 1 starts (time T0), the gate driver 15b selects the OFF-state voltage Voff, and applies the OFF-state voltage Voff1 to the lines L1 to Lx of the scan lines 5. The upper part of FIG. 20 shows a timing chart for the ON-state voltage Von. The middle part thereof shows a timing chart for the OFF-state voltage Voff. The lower part thereof shows a timing chart for a voltage value V5 which is applied to the scan lines 5 as a result of the ON-state voltage Von and the OFF-state voltage Voff being switched. The voltage value V5 is the ON-state voltage Von or the OFF-state voltage Voff to which the gate driver 15b selectively switches at each point of time.

After the gate driver 15b applies the OFF-state voltage Voff1 to the gate electrodes 8g of the TFTs 8 to close the gates of the TFTs 8 as described above, the gate driver 15b performs the reset processing of the radiation detection elements 7. That is, the gate driver 15b switches to the ON-state voltage Von at the time T1, applies the ON-state voltage Von1 having the highest predetermined positive voltage value to the TFTs 8 all at once so as to open the gates of all the TFTs 8, and discharges and removes the excess charge such as dark charge accumulated in the radiation detection elements 7 therefrom to the signal lines 6 and the bias lines 9.

Then, as described above, after a predetermined time elapses, the power supply circuit 15a of the scan driving section 15 decreases the ON-state voltage Von applied to the gate electrodes 8g of the TFTs 8 from the ON-state voltage Von1 to the ON-state voltage Von2 having a lower predetermined voltage value all at once at the time T2. Then, the scan driving section 15 keeps the ON-state voltage Von2, and waits for the start of the irradiation. The power supply circuit 15a increases the OFF-state voltage Voff, which is not yet connected to the lines L1 to Lx of the scan lines 5 at this point of time, from the OFF-state voltage Voff1 having the lowest predetermined voltage value to the OFF-state voltage Voff2. In the embodiment, the OFF-state voltage Voff2 is set at 0[V].

The control section 2 turns off the switch 43d (shown in FIG. 9) of the current detection section 43 at this point of time in order to detect the start of the irradiation, and supplies power from the power supply section 44 to the differential amplifier 43c to start the current detection section 43.

As shown in FIG. 12, when irradiation starts to the radiation image capturing device 1 at the time t1, the charge (electron-hole pairs) generated by irradiation in the radiation detection elements 7 are discharged to the bias lines 9 and the signal lines 6 as described above. Consequently, the voltage value V corresponding to the current outputted from the differential amplifier 43c of the current detection section 43 starts to increase at the time t1.

When the voltage value V outputted from the current detection section 43 increases, and for example, the voltage value V exceeds a preset threshold value, or the increase rate of the voltage value V exceeds a preset threshold value, the control section 22 detects that the irradiation starts. In FIG. 20, the above-described condition is satisfied at the time T3, and hence the start of the irradiation is detected thereat.

When the control section 22 detects the start of the irradiation at the time T3, the gate driver 15b of the scan driving section 15 switches the voltage applied to the gate electrodes 8g of the TFTs 8 via the lines L1 to Lx of the scan lines 5 from the ON-state voltage Von2 to the OFF-state voltage Voff2 having the voltage value increased all at once as described above (i.e. 0[V] in the third embodiment).

Right after that, at a time T4, the gate driver 15b decreases the OFF-state voltage Voff2 to the OFF-state voltage Voff1 having the lowest predetermined negative voltage value all at once so as to close the gates of all the TFTs 8 completely, and switches the radiation detection elements 7 to the charge accumulation mode. As shown in FIG. 12, when the start of the irradiation is detected and the voltage applied to the gate electrodes 8g of the TFTs 8 is switched to the OFF-state voltage Voff2 at the time T3, the current flowing in the bias lines 9 and the connection line 10 rapidly decreases.

As a preparation for the reading processing of image data from the radiation detection elements 7 performed thereafter, the power supply circuit 15a increases the ON-state voltage Von, which is blocked to be connected to the lines L1 to Lx of the scan lines 5, to the ON-state voltage Von1 having the highest predetermined positive voltage value. The control section 22 turns on the switch 43d of the current detection section 43 to short-circuit the terminals of the resistor 43a, and also stops supplying power from the power supply section 44 to the differential amplifier 43c to stop the operation of the current detection section 43.

Thus, when the voltage applied to the lines L1 to Lx of the scan lines 5 is switched from the ON-state voltage Von2 to the OFF-state voltage Voff2 at the time T3, the voltage value of the ON-state voltage Von2 is sufficiently low, and the difference $\Delta V$ (shown at the lower part of FIG. 20) between the voltage value of the ON-state voltage Von2 and the voltage value of the OFF-state voltage Voff2 (i.e. 0[V], in the embodiment) is sufficiently low. Accordingly, the drive circuit in the gate driver 15 is not overloaded, and hence the gate driver 15b can be prevented from being damaged or broken.

However, as described above, in the third embodiment, the ON-state voltage Von2 is defined by the current amount i leak of the leak current flowing in the radiation detection elements 7. Therefore, the ON-state voltage Von2 cannot be always set at a sufficiently low voltage value.

Figure 21A:
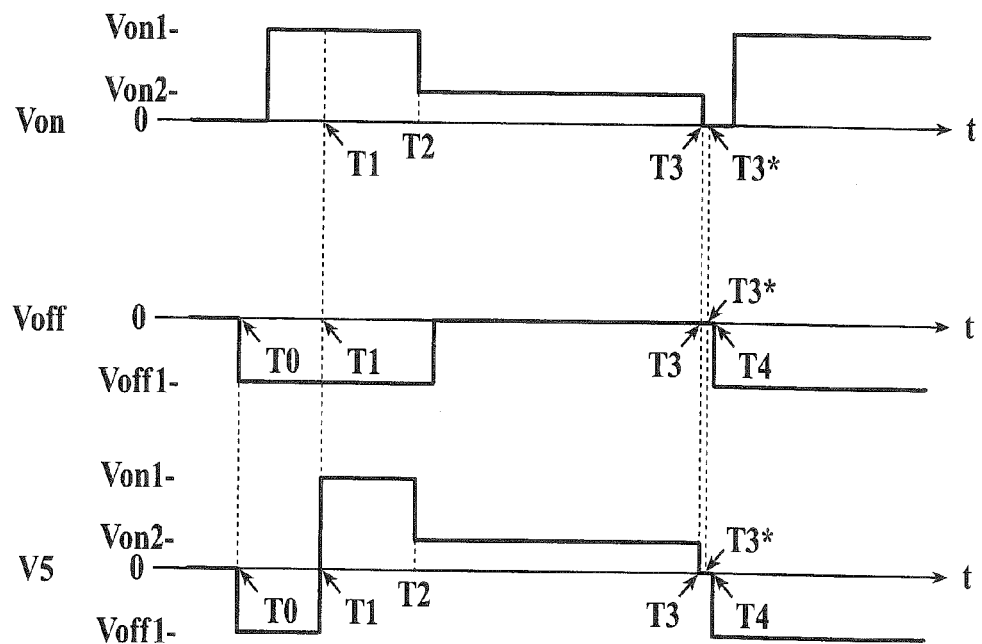
FIG. 21A shows examples of a timing chart of an ON-state voltage (upper part) and an OFF-state voltage (middle part) in the reset processing or the like of each radiation detection element, and a voltage value applied to each scan line by switching the ON-state voltage and the OFF-state voltage (lower part)

In such a case, as shown in FIG. 21A, when the control section 22 detects the start of the irradiation at the time T3, the ON-state voltage Von is further decreased, for example, to the ON-state voltage Von4 having a further lower voltage value of 0[V] or the like. After that, at a time T3*, the ON-state voltage Von4 is switched to the OFF-state voltage Voff2 having the increased voltage value of 0[V], which is set in a manner descried above, or the like all at once. Right after that, at the time T4, the OFF-state voltage Voff2 is decreased to the OFF-state voltage Voff1 having the lowest predetermined negative voltage value all at once so as to close the gates of the TFTs 8 completely.

Figure 21B:
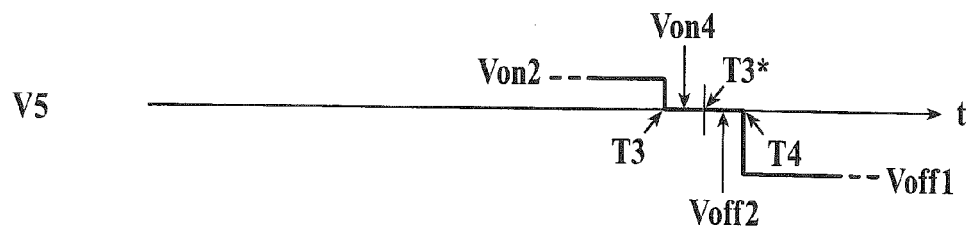
FIG. 21B is an enlarged view of the timing chart shown at the lower part of FIG. 21A.

The upper part of FIG. 21A shows a timing chart for the ON-state voltage Von. The middle part thereof shows a timing chart for the OFF-state voltage Voff. The lower part thereof shows a timing chart for the voltage value V5 which is applied to the scan lines 5 as a result of the ON-state voltage Von and the OFF-state voltage Voff being switched. FIG. 21B is an enlarged view of the timing chart for the voltage value V5 shown at the lower part of FIG. 21A. A part around the time T3* of FIG. 21A is enlarged in a time axis direction in FIG. 21B.

By having such a configuration, for example, the ON-state voltage Von4 set at 0[V] or the like can be switched to the OFF-state voltage Voff2 set at 0[V] or the like. Consequently, the difference ΔV between the voltage value of the before-switched ON-state voltage Von4 and the voltage value of the after-switched OFF-state voltage Voff2 is 0 or a very small difference. Accordingly, the drive circuit in the gate driver 15b is not overloaded, and hence the gate driver 15b can be prevented from being damaged or broken.

Furthermore, when the further-decreased voltage value of the ON-state voltage Von4 and the increased voltage value of the OFF-state voltage Voff2 are both set at 0[V] as described above, the drive circuit in the gate driver 15b is not overloaded at all, and hence the gate driver 15b can be prevented from being damaged or broken for certain.

However, it is not necessary to set both the voltage value of the ON-state voltage Von4 and the voltage value of the OFF-state voltage Voff2 at 0[V]. For example, the voltage value of the ON-state voltage Von4 may be set at a small positive value, and the voltage value of the OFF-state voltage Voff2 may be set at 0[V]. Alternatively, the voltage value of the ON-state voltage Von4 may be set at 0[V], and the voltage value of the OFF-state voltage Voff2 may be set at a negative value smaller than 0[V]. Then, the difference ΔV between the voltage values thereof can be still a very small difference. Accordingly, the gate driver 15b can be appropriately prevented from being overloaded.

As long as the voltage values of the ON-state voltage Von4 and the OFF-state voltage Voff2 do not make the gate driver 15b overloaded, the voltage values thereof can be appropriately set.

As described above, according to the radiation image capturing device 1 of the third embodiment, after the ON-state voltage Von1 having the highest predetermined positive voltage value is applied to the gate electrodes 8g of the TFTs 8 in the reset processing of the radiation detection elements 7, the ON-state voltage Von is decreased to the ON-state voltage Von2, and after the irradiation starts, the ON-state voltage Von2 having the decreased voltage value or the ON-state voltage Von4 having the further-decreased voltage value from the decreased voltage value of the ON-state voltage Von2 is switched to the OFF-state voltage Voff2 having the increased voltage value. After that, the voltage value of the OFF-state voltage Voff is decreased to the predetermined negative voltage value of the OFF-state voltage Voff1 which is the original OFF-state voltage Voff.

Consequently, when the start of the irradiation is detected, and the voltage applied to the gate electrodes 8g of the TFTs 8 via the lines L1 to Lx of the scan lines 5 is switched from the ON-state voltage Von to the OFF-state voltage Voff, the difference ΔV between the decreased voltage value of the ON-state voltage Von2 or the further-decreased voltage value of the ON-state voltage Von4, the further-decreased voltage value being further decreased from the decreased voltage value of the ON-state voltage Von2, and the increased voltage value of the OFF-state voltage Voff2 can be 0 or a very small difference. Accordingly, the gate driver 15b of the scan driving section 15 can be appropriately prevented from being overloaded, and hence the gate driver 15 can be appropriately prevented from being damaged or broken.

As described above, the gate driver 15b of the scan driving section 15 of the embodiment is constituted of the gate ICs 12a (shown in FIG. 6) or the like. However, of the gate ICs 12a, there may be gate ICs 12a which, even when a signal is transmitted to the gate ICs 12a to switch the voltage applied to the lines L1 to Lx of the scan lines 5 from one to another at the same time, makes the timing different little by little with respect to each of the lines L1 to Lx of the scan lines 5 so as to apply the voltage thereto, the timing at which the voltage applied thereto is switched from one to another.

This is a configuration to prevent the functional components of the radiation image capturing device 1 from being overloaded, which may occur when the voltage applied to the lines L1 to Lx of the scan lines 5 is switched from the ON-state voltage Von to the OFF-state voltage Voff at the same time and all at once, and accordingly to prevent the functional components thereof from being damaged or the like.

However, when the voltage applied to the lines L1 to Lx of the scan lines 5 is not switched from the ON-state voltage Von to the OFF-state voltage Voff all at once and at the same time, namely, when the timing at which the voltage applied thereto is switched is made to be different with respect to each of the lines L1 to Lx of the scan lines 5 even little by little, the switching timing of on/off of the TFTs 8 connected to each of the lines L1 to Lx of the scan lines 5 is made to be different.

When the switching timing of on/off of the TFTs 8 is made to be different with respect to each of the lines L1 to Lx of the scan lines 5, the later the timing is, the timing at which the voltage applied to the gate electrodes 8g of the TFTs 8 is switched to the OFF-state voltage Voff, the more often the weak current generated in the signal lines 6 or the like, which is a transitory phenomenon accompanying the voltage switching, flows into the radiation detection elements 7 via the TFTs 8, for example. As a result, the remaining amounts of charge in the radiation detection elements 7 at the time when the TFTs 8 are turned off differ.

When the initial remaining amounts of charge in the radiation detection elements 7 at the time when the TFTs 8 are turned off differ, its influence remains even if image correction such as offset correction is performed thereafter, and bad influence may be exerted on a radiation image obtained at the end.

The above problem can be solved by using gate ICs 12a which are made in such a way as not to make the timing, at which the voltage is switched, different when receiving a signal which instructs to switch the voltage applied to each of the lines L1 to Lx of the scan lines 5 from one to another at the same time; and to switch the voltage with respect to each of the lines L1 to Lx of the scan lines 5 at the same time. However, there is a case where such gate ICs 12a cannot be used.

In that case, it is possible to use the gate ICs 12a making the timing at which the voltage is switched different a little; adjust the timing to be the same by the following method or the like; and switch the voltage applied to the lines L1 to Lx of the scan lines 5 from the gate ICs 12a of the gate driver 15b, from the ON-state voltage Von to the OFF-state voltage Voff at the same time and all at once.

Figure 22:
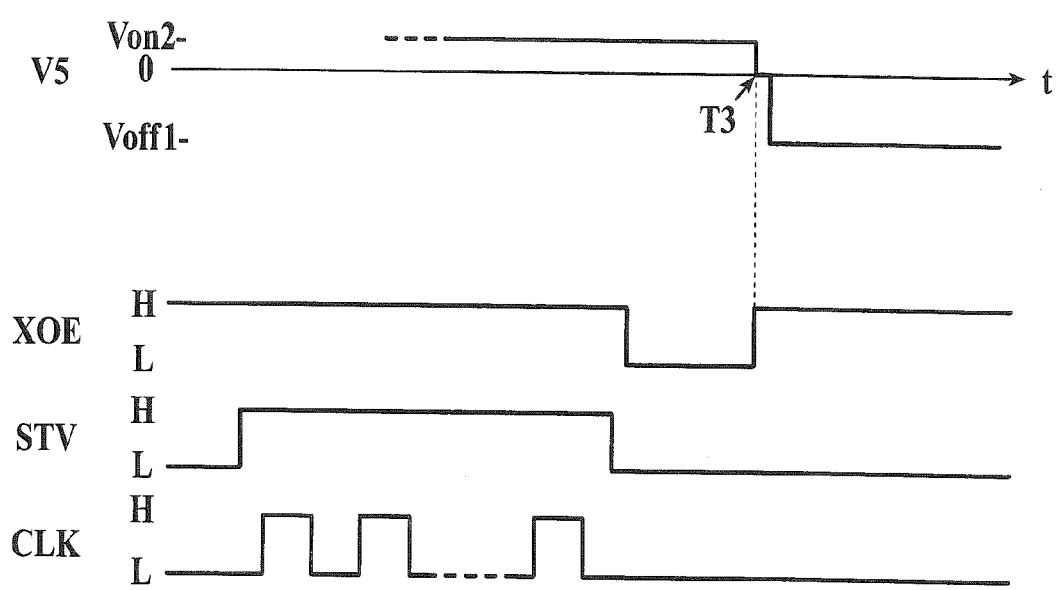
FIG. 22 is a timing chart of a voltage value applied to each scan line, an enable signal, a signal inputted into a shift register, and a clock, in a method in which a voltage applied to each scan line from a gate IC is switched from the ON-state voltage to the OFF-state voltage at the same time.

That is, before the ON-state voltage Von is switched to the OFF-state voltage Voff, for example, an H (high) signal (STV) is transmitted to a not-shown shift register having addresses for the number of scan lines 5 connected to the gate ICs 12a, in response to a clock (CLK) as shown in FIG. 22, so as to be consecutively inputted into the addresses of the shift register.

As described above, when the gate ICs 12a respond to the ordinal signal instructing to switch the voltage applied to each of the lines L1 to Lx of the scan lines 5 at the same time, the gate ICs 12a switch the voltage by making the timing different a little. Hence, the ordinal signal is switched to an enable signal (XOE), for example.

In the case shown in FIG. 22, the enable signal is low active, and when the enable signal is L (low), the H signal inputted in each of the addresses of the shift register is transmitted to channels of the gate ICs 12a, and the ON-state voltage Von is applied to the lines L1 to Lx of the scan lines 5 from the gate ICs 12a. When the enable signal is H (high), the OFF-state voltage Voff is applied to the lines L1 to Lx of the scan lines 5 from the gate ICs 12a.

By switching the ordinal signal to the enable signal, the operation state of the gate ICs 12a is taken over from the state in which the gate ICs 12a operate in response to the ordinal signal to the state in which the gate ICs 12a operate in response to the enable signal. By switching the voltage when the enable signal is L (low) signal, the state in which the ON-state voltage Von2 is applied to the lines L1 to Lx of the scan lines 5 from the gate ICs 12a is kept.

By switching the enable signal from L (low) to H (high) when the control section 22 detects the start of the irradiation, the voltage applied to the lines L1 to Lx of the scan lines 5 is switched from the ON-state voltage Von2 (or the ON-state voltage Von4) to the OFF-state voltage Voff2. In this case, when the enable signal (XOE) is switched from L (low) to H (high), the voltage applied to the lines L1 to Lx of the scan lines 5 is switched from the ON-state voltage Von2 (or the ON-state voltage Von4) to the OFF-state voltage Voff2 at the same time and all at once without the timing difference.

Thus, the above-described problem can be solved. Furthermore, in this case, even when the voltage applied to the lines L1 to Lx of the scan lines 5 is switched from the ON-state voltage Von2 (or the ON-state voltage Von4) to the OFF-state voltage Voff2 at the same time and all at once, as long as the difference ΔV between the voltage value of the before-switched ON-state voltage Von2 or Von4 and the voltage value of the after-switched OFF-state voltage Voff2 is set to be a very small value or 0 as described above, the functional components of the radiation image capturing device 1 can be prevented from being overloaded, and hence the functional components thereof can be prevented from being damaged or the like.

INDUSTRIAL APPLICABILITY

The present invention is applicable to the field where radiation image capturing is performed (in particular, in the field of medical services).

EXPLANATION OF REFERENCES

1 radiation image capturing device
5 scan line
6 signal line
7 radiation detection element
8 TFT (switch section)
9 bias line
14 bias power supply
15 scan driving section
15a power supply circuit
15b gate driver
17 reading circuit
18 amplifier circuit
18a operational amplifier
18e variable resistor
22 control section
43 current detection section
i leak current amount of leak current
P detection section
r region
V voltage value corresponding to current (current value)
Vbias bias voltage
Voff OFF-state voltage
Voff1 OFF-state voltage having predetermined negative voltage value
Voff2 OFF-state voltage having increased voltage value
Von ON-state voltage
Von1 ON-state voltage having predetermined voltage value
Von2 ON-state voltage having decreased voltage value
Von3 ON-state voltage having voltage value increased from Von2 with predetermined voltage width
Von4 ON-state voltage having further decreased voltage value
ΔV difference

The invention claimed is:

1. A radiation image capturing device comprising:
a detection section including:
   a plurality of scan lines;
   a plurality of signal lines arranged to intersect the scan lines; and
   a plurality of radiation detection elements two-dimensionally and respectively arranged in a plurality of regions divided by the scan lines and the signal lines;
a switch section provided for each of the radiation detection elements, wherein when an ON-state voltage is applied to the scan lines to which the switch section is connected, the switch section discharges electric charge generated in the radiation detection elements, and when an OFF-state voltage is applied to the connected scan lines, the switch section accumulates the electric charge in the radiation detection elements, the electric charge being generated in the radiation detection elements;
a scan driving section including:
   a gate driver which applies a voltage to the switch section via each of the scan lines; and
   a power supply circuit which supplies the voltage to the gate driver;
a current detection section which detects a current flowing in the device by irradiation; and
a control section which detects at least a start of the irradiation based on a current value of the current detected by the current detection section, wherein
the control section applies the ON-state voltage having a predetermined voltage value from the scan driving section to the switch section via each of the scan lines simultaneously so as to perform reset processing of each of the radiation detection elements before radiation image capturing, and thereafter, decreases the voltage value of the ON-state voltage simultaneously, monitors the current value outputted from the current detection section while keeping the decreased voltage value of the ON-state voltage, and waits for the start of the irradiation.

2. The radiation image capturing device according to claim 1, wherein
the power supply circuit of the scan driving section has a function to adjust the voltage value of the ON-state voltage, or
the radiation image capturing device further comprises a section which adjusts the voltage value of the ON-state voltage, separately from the power supply circuit.

3. The radiation image capturing device according to claim 1, wherein the decreased voltage value of the ON-state voltage is set at a voltage value with which a current value of an ON-state current flowing in the switch section becomes more than a current amount of a leak current flowing in the radiation detection elements.

4. The radiation image capturing device according to claim 1 further comprising:
a bias line connected to each of the radiation detection elements; and
a bias power supply which applies a bias voltage to each of the radiation detection elements via the bias line, wherein
the current detection section detects a current value of a current flowing in the bias line.

5. The radiation image capturing device according to claim 1, wherein when the control section detects the start of the irradiation, the control section switches the voltage applied to the switch section via each of the scan lines to the OFF-state voltage simultaneously.

6. The radiation image capturing device according to claim 1, wherein after the control section decreases the voltage value of the ON-state voltage applied from the scan driving section to the switch section via each of the scan lines simultaneously, the control section performs an operation to increase and decrease the decreased voltage value of the ON-state voltage with a predetermined voltage width one time or a plurality of times before the control section detects the start of the irradiation based on the current value detected by the current detection section.

7. The radiation image capturing device according to claim 1 further comprising:
a reading section including an amplifier circuit which, via the switch section and the signal lines, reads the electric charge accumulated in each of the radiation detection elements from each of the radiation detection elements, and converts the electric charge into image data, wherein
the amplifier circuit includes an operational amplifier, an input terminal of which is connected to the signal lines via a variable resistor, and an output terminal of which outputs the image data, and
at least while the control section monitors the current value outputted from the current detection section and waits for the start of the irradiation in a state in which the control section decreases the voltage value of the ON-state voltage simultaneously after the reset processing of each of the radiation detection elements, a resistance value of the variable resistor varies to be in a low state.

8. The radiation image capturing device according to claim 1, wherein
when the control section detects the start of the irradiation, the scan driving section switches the ON-state voltage having the decreased and kept voltage value to the OFF-state voltage having the increased voltage value, and thereafter, decreases the increased voltage value of the OFF-state voltage to a predetermined negative voltage value, and
a difference between the decreased voltage value of the ON-state voltage and the increased voltage value of the OFF-state voltage is set at a difference with which the gate driver of the scan driving section is not damaged or broken when the ON-state voltage is switched to the OFF-state voltage.

9. The radiation image capturing device according to claim 8, wherein
when the control section detects the start of the irradiation, the scan driving section further decreases the decreased and kept voltage of the ON-state voltage, and thereafter, switches to the OFF-state voltage having the increased voltage value, and
a difference between the further decreased voltage value of the ON-state voltage and the increased voltage value of the OFF-state voltage is set at a difference with which the gate driver of the scan driving section is not damaged or broken when the ON-state voltage is switched to the OFF-state voltage.

10. The radiation image capturing device according to claim 9, wherein the further decreased voltage value of the ON-state voltage is set at 0[V].

11. The radiation image capturing device according to claim 8, wherein the increased voltage value of the OFF-state voltage is set at 0[V].

12. The radiation image capturing device according to claim 8, wherein
the power supply circuit of the scan driving section has a function to adjust the voltage value of the ON-state voltage and the voltage value of the OFF-state voltage, or
the radiation image capturing device further comprises a section which adjusts the voltage value of the ON-state voltage and the voltage value of the OFF-state voltage, separately from the power supply circuit.

* * * * *